United States Patent
Rosen et al.

(10) Patent No.: US 11,886,046 B2
(45) Date of Patent: Jan. 30, 2024

(54) MULTI-REGION REFRACTIVE LENSES FOR VISION TREATMENT

(71) Applicant: AMO Groningen B.V., Groningen (NL)

(72) Inventors: Robert Rosen, Groningen (NL); Franck Gounou, Groningen (NL)

(73) Assignee: AMO Groningen B.V., Groningen (NL)

(*) Notice: Subject to any disclaimer, the term of this patent is extended or adjusted under 35 U.S.C. 154(b) by 403 days.

(21) Appl. No.: 17/103,922

(22) Filed: Nov. 24, 2020

(65) Prior Publication Data

US 2021/0199989 A1 Jul. 1, 2021

Related U.S. Application Data

(60) Provisional application No. 62/955,327, filed on Dec. 30, 2019.

(51) Int. Cl.
*A61F 2/16* (2006.01)
*G02C 7/06* (2006.01)
*G02C 7/02* (2006.01)

(52) U.S. Cl.
CPC ............. *G02C 7/06* (2013.01); *G02C 7/022* (2013.01); *A61F 2/1613* (2013.01)

(58) Field of Classification Search
None
See application file for complete search history.

(56) References Cited

U.S. PATENT DOCUMENTS

| | | |
|---|---|---|
| 2,077,092 A | 4/1937 | Broder |
| 3,305,294 A | 2/1967 | Alvarez |
| 3,367,734 A | 2/1968 | Karl et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |

(Continued)

FOREIGN PATENT DOCUMENTS

| | | |
|---|---|---|
| AU | 735664 B2 | 7/2001 |
| AU | 2010212408 A1 | 9/2010 |

(Continued)

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.

(Continued)

*Primary Examiner* — Javier G Blanco

(74) *Attorney, Agent, or Firm* — Johnson & Johnson Surgical Vision, Inc.

(57) ABSTRACT

Apparatuses, systems and methods for providing improved ophthalmic lenses, particularly intraocular lenses (IOLs), include features for vertex matching distance regions of such lenses. Exemplary ophthalmic lenses can include an optic disposed about an optical axis and having a refractive profile including a region having an add power and a first distance region and a second distance region extending outward from the first distance region and being vertex matched with the first distance region.

10 Claims, 12 Drawing Sheets

(56) References Cited

U.S. PATENT DOCUMENTS

| | | |
|---|---|---|
| 4,162,122 A | 7/1979 | Cohen |
| 4,174,543 A | 11/1979 | Kelman |
| 4,210,391 A | 7/1980 | Cohen et al. |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert, Jr. |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,564,484 A | 1/1986 | Neefe |
| 4,580,882 A | 4/1986 | Nuchman et al. |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | LeMaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,769,033 A | 9/1988 | Nordan |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,906,246 A | 3/1990 | Grendahl |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,050,981 A | 9/1991 | Roffman |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,112,351 A | 5/1992 | Christie et al. |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,181,053 A | 1/1993 | Brown |
| 5,184,405 A | 2/1993 | Cress |
| 5,191,366 A | 3/1993 | Kashiwagi |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,220,359 A | 6/1993 | Roffman |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,270,744 A | 12/1993 | Portney |
| 5,278,592 A | 1/1994 | Marie et al. |
| 5,384,606 A | 1/1995 | Koch et al. |
| 5,387,970 A | 2/1995 | Neubert et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,485,228 A | 1/1996 | Roffman et al. |
| 5,521,656 A | 5/1996 | Portney |
| 5,567,365 A | 10/1996 | Weinschenk, III et al. |
| 5,571,177 A | 11/1996 | Deacon et al. |
| 5,589,024 A | 12/1996 | Blake |
| 5,620,720 A | 4/1997 | Glick et al. |
| 5,628,796 A | 5/1997 | Suzuki |
| 5,652,638 A | 7/1997 | Roffman et al. |
| 5,657,108 A | 8/1997 | Portney |
| 5,684,560 A | 11/1997 | Roffman et al. |
| 5,691,800 A | 11/1997 | Iki et al. |
| 5,699,142 A | 12/1997 | Lee et al. |
| 5,715,031 A | 2/1998 | Roffman et al. |
| 5,716,403 A | 2/1998 | Tran et al. |
| 5,748,282 A | 5/1998 | Freeman |
| 5,754,270 A | 5/1998 | Rehse et al. |
| 5,760,871 A | 6/1998 | Kosoburd et al. |
| 5,766,244 A | 6/1998 | Binder |
| 5,777,719 A | 7/1998 | Williams et al. |
| 5,796,462 A | 8/1998 | Roffman et al. |
| 5,798,817 A * | 8/1998 | de Carle ............... G02C 7/042 |
| | | 351/159.41 |
| 5,801,807 A | 9/1998 | Satake et al. |
| 5,864,378 A | 1/1999 | Portney |
| 5,864,379 A | 1/1999 | Dunn |
| 5,877,839 A | 3/1999 | Portney |
| 5,895,422 A | 4/1999 | Hauber |
| 5,919,229 A | 7/1999 | Portney |
| 5,928,282 A | 7/1999 | Nigam |
| 5,968,094 A | 10/1999 | Werblin et al. |
| 6,007,747 A | 12/1999 | Blake et al. |
| 6,015,435 A | 1/2000 | Valunin et al. |
| 6,024,447 A | 2/2000 | Portney |
| 6,030,077 A | 2/2000 | Sawano et al. |
| 6,051,024 A | 4/2000 | Cumming |
| 6,055,111 A | 4/2000 | Nomura et al. |
| 6,082,856 A | 7/2000 | Dunn et al. |
| 6,086,203 A | 7/2000 | Blum et al. |
| 6,106,118 A | 8/2000 | Menezes et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,176,579 B1 | 1/2001 | Mandell |
| 6,179,870 B1 | 1/2001 | Sourdille et al. |
| 6,186,625 B1 | 2/2001 | Portney |
| 6,210,005 B1 | 4/2001 | Portney |
| 6,221,105 B1 | 4/2001 | Portney |
| 6,224,211 B1 | 5/2001 | Gordon |

(56) References Cited

U.S. PATENT DOCUMENTS

| | | |
|---|---|---|
| 6,235,055 B1 | 5/2001 | Chu |
| 6,260,966 B1 | 7/2001 | Sawano et al. |
| 6,261,321 B1 | 7/2001 | Kellan |
| 6,286,956 B1 | 9/2001 | Oyama et al. |
| 6,319,282 B1 | 11/2001 | Nishi |
| 6,325,509 B1 | 12/2001 | Hodur et al. |
| 6,338,559 B1 | 1/2002 | Williams et al. |
| 6,390,622 B1 | 5/2002 | Muckenhirn et al. |
| 6,409,339 B1 | 6/2002 | Wanders |
| 6,409,340 B1 | 6/2002 | Portney |
| 6,419,697 B1 | 7/2002 | Kelman |
| 6,428,573 B2 | 8/2002 | Barnett |
| 6,454,408 B1 | 9/2002 | Morris et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,511,178 B1 | 1/2003 | Roffman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,540,353 B1 | 4/2003 | Dunn |
| 6,547,822 B1 | 4/2003 | Lang |
| 6,554,859 B1 | 4/2003 | Lang et al. |
| 6,557,992 B1 | 5/2003 | Dwyer et al. |
| 6,596,025 B2 | 7/2003 | Portney |
| 6,598,606 B2 | 7/2003 | Terwee et al. |
| 6,609,793 B2 | 8/2003 | Norrby et al. |
| 6,638,305 B2 | 10/2003 | Laguette |
| 6,663,240 B2 | 12/2003 | Patel |
| 6,705,729 B2 | 3/2004 | Piers et al. |
| 6,709,102 B2 | 3/2004 | Duppstadt |
| 6,764,179 B2 | 7/2004 | Sakai et al. |
| 6,797,003 B1 | 9/2004 | Blake et al. |
| 6,802,605 B2 | 10/2004 | Cox et al. |
| 6,808,262 B2 | 10/2004 | Chapoy et al. |
| 6,814,439 B2 | 11/2004 | Portney |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,871,953 B1 | 3/2005 | Mandell et al. |
| 6,874,887 B2 | 4/2005 | Tyson |
| 6,883,915 B2 | 4/2005 | Ye et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,004,585 B2 | 2/2006 | Lindacher |
| 7,018,409 B2 | 3/2006 | Glick et al. |
| 7,036,931 B2 | 5/2006 | Lindacher et al. |
| 7,040,757 B2 | 5/2006 | Hall et al. |
| 7,048,760 B2 | 5/2006 | Cumming |
| 7,052,133 B2 | 5/2006 | Lindacher et al. |
| 7,061,693 B2 | 6/2006 | Zalevsky |
| 7,073,906 B1 | 7/2006 | Portney |
| 7,080,906 B2 | 7/2006 | Lindacher et al. |
| 7,137,702 B2 | 11/2006 | Piers et al. |
| 7,156,516 B2 | 1/2007 | Morris et al. |
| 7,178,918 B2 | 2/2007 | Griffin |
| 7,188,949 B2 | 3/2007 | Bandhauer et al. |
| 7,204,849 B2 | 4/2007 | Portney |
| 7,241,311 B2 | 7/2007 | Norrby et al. |
| 7,287,852 B2 | 10/2007 | Fiala |
| 7,293,873 B2 | 11/2007 | Dai et al. |
| 7,365,917 B2 | 4/2008 | Zalevsky |
| 7,370,962 B2 | 5/2008 | Roffman et al. |
| 7,377,640 B2 | 5/2008 | Piers et al. |
| 7,381,221 B2 | 6/2008 | Lang et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,002,827 B2 | 8/2011 | Deacon et al. |
| 8,018,164 B2 | 9/2011 | Shannon et al. |
| 8,042,942 B2 | 10/2011 | Kaga et al. |
| 8,147,062 B2 | 4/2012 | Kaga et al. |
| 8,162,477 B2 | 4/2012 | Carimalo et al. |
| 8,231,219 B2 | 7/2012 | Weeber |
| 8,240,847 B2 | 8/2012 | Holden et al. |
| 8,241,354 B2 | 8/2012 | Hong et al. |
| 8,382,281 B2 | 2/2013 | Weeber |
| 8,430,508 B2 | 4/2013 | Weeber |
| 8,480,228 B2 | 7/2013 | Weeber |
| 8,486,141 B2 | 7/2013 | Lang et al. |
| 8,529,559 B2 | 9/2013 | Liang |
| 8,573,775 B2 | 11/2013 | Weeber |
| 8,632,187 B1 | 1/2014 | Franques et al. |
| 8,647,383 B2 | 2/2014 | Sanger et al. |
| 8,672,472 B2 | 3/2014 | Holden et al. |
| 8,672,474 B2 | 3/2014 | Lindacher et al. |
| 8,747,466 B2 | 6/2014 | Weeber et al. |
| 8,770,745 B2 | 7/2014 | Lindacher et al. |
| 8,857,982 B2 | 10/2014 | Franques et al. |
| 8,862,447 B2 | 10/2014 | Weeber |
| 8,894,706 B2 | 11/2014 | Portney |
| 8,974,526 B2 | 3/2015 | Bogaert |
| 9,039,172 B2 | 5/2015 | Lindacher et al. |
| 9,265,603 B2 | 2/2016 | Sanger et al. |
| 9,335,563 B2 | 5/2016 | Weeber |
| 9,477,097 B2 | 10/2016 | Holden et al. |
| 10,028,825 B2 | 7/2018 | Canovas et al. |
| 10,426,601 B2 | 10/2019 | Canovas Vidal et al. |
| 10,437,078 B2 | 10/2019 | Canovas Vidal et al. |
| 10,709,550 B2 | 7/2020 | Canovas et al. |
| 11,452,595 B2 | 9/2022 | Bogaert |
| 11,506,914 B2 | 11/2022 | Canovas Vidal et al. |
| 2001/0035935 A1 | 11/2001 | Bhalakia et al. |
| 2001/0051825 A1 | 12/2001 | Peterson |
| 2002/0063848 A1 | 5/2002 | Fiala |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0054358 A1 | 3/2004 | Cox et al. |
| 2004/0068317 A1 | 4/2004 | Knight |
| 2004/0111153 A1 | 6/2004 | Woods et al. |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2004/0207807 A1 | 10/2004 | Lindacher |
| 2004/0237971 A1 | 12/2004 | Radhakrishnan et al. |
| 2004/0246440 A1 | 12/2004 | Andino et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |

(56) References Cited

U.S. PATENT DOCUMENTS

| | | |
|---|---|---|
| 2007/0182924 A1 | 8/2007 | Hong et al. |
| 2007/0258143 A1 | 11/2007 | Portney |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051870 A1 | 2/2009 | Lindacher et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0279048 A1 | 11/2009 | Hong et al. |
| 2009/0303433 A1 | 12/2009 | Shimojo |
| 2009/0323020 A1 | 12/2009 | Zhao et al. |
| 2010/0016965 A1 | 1/2010 | Hong et al. |
| 2010/0036489 A1 | 2/2010 | Lindacher et al. |
| 2010/0066973 A1 | 3/2010 | Portney |
| 2010/0082017 A1 | 4/2010 | Zickler et al. |
| 2010/0097569 A1 | 4/2010 | Weeber et al. |
| 2010/0100178 A1 | 4/2010 | Weeber et al. |
| 2010/0161048 A1 | 6/2010 | Schaper, Jr. |
| 2010/0161051 A1 | 6/2010 | Hong |
| 2010/0234943 A1 | 9/2010 | Portney |
| 2010/0315589 A1 | 12/2010 | Portney |
| 2011/0149236 A1 | 6/2011 | Weeber |
| 2011/0157548 A1 | 6/2011 | Lesage et al. |
| 2012/0140166 A1 | 6/2012 | Zhao |
| 2012/0143326 A1 | 6/2012 | Canovas et al. |
| 2012/0320334 A1 | 12/2012 | Ho et al. |
| 2014/0135919 A1 | 5/2014 | Gontijo et al. |
| 2015/0182329 A1 | 7/2015 | Bogaert |
| 2015/0297343 A1 | 10/2015 | Hehn |
| 2015/0342727 A1 | 12/2015 | Fernández et al. |
| 2016/0062144 A1 | 3/2016 | Brennan et al. |
| 2016/0062145 A1 | 3/2016 | Brennan et al. |
| 2016/0299355 A1 | 10/2016 | Biemold et al. |
| 2017/0216020 A1 | 8/2017 | Weeber et al. |
| 2019/0004221 A1 | 1/2019 | Weeber et al. |
| 2020/0022806 A1 | 1/2020 | Carmen et al. |
| 2020/0330218 A1 | 10/2020 | Carmen et al. |
| 2023/0014535 A1 | 1/2023 | Bogaert |

FOREIGN PATENT DOCUMENTS

| | | |
|---|---|---|
| AU | 2012362545 B2 | 7/2015 |
| CA | 2722274 A1 | 10/2009 |
| CA | 2787997 C | 2/2015 |
| CA | 2901889 A1 | 2/2016 |
| CN | 1035363 A | 9/1989 |
| CN | 1406120 A | 3/2003 |
| CN | 1833192 A | 9/2006 |
| DE | 8107675 U1 | 7/1981 |
| EP | 226400 A2 | 6/1987 |
| EP | 227357 A2 | 7/1987 |
| EP | 900403 A1 | 3/1999 |
| EP | 0926531 A1 | 6/1999 |
| EP | 957331 A2 | 11/1999 |
| EP | 1310267 B1 | 1/2008 |
| EP | 1424049 B1 | 6/2009 |
| FR | 2745711 A1 | 9/1997 |
| JP | 4126144 A2 | 4/1992 |
| JP | 2004537332 A | 12/2004 |
| NO | 2009029515 A1 | 3/2009 |
| WO | 8603961 A1 | 7/1986 |
| WO | 8700299 A1 | 1/1987 |
| WO | 809950 A1 | 12/1988 |
| WO | 9222000 A1 | 12/1992 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 0008516 A1 | 2/2000 |
| WO | 0019906 A1 | 4/2000 |
| WO | 0027315 A1 | 5/2000 |
| WO | 0111418 A1 | 2/2001 |
| WO | 0118592 A1 | 3/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 02074210 A2 | 9/2002 |
| WO | 02084381 A2 | 10/2002 |
| WO | 03009053 A1 | 1/2003 |
| WO | 02084381 A3 | 10/2003 |
| WO | 2004034129 A1 | 4/2004 |
| WO | 2004068214 A1 | 8/2004 |
| WO | 04089252 A2 | 10/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009017403 A1 | 2/2009 |
| WO | 2009020963 A1 | 2/2009 |
| WO | 2009058755 A1 | 5/2009 |
| WO | 2009076670 A1 | 6/2009 |
| WO | 2009137491 A1 | 11/2009 |
| WO | 2010009254 A1 | 1/2010 |
| WO | 2010009257 A1 | 1/2010 |
| WO | 2010054255 A1 | 5/2010 |
| WO | 2013018379 A1 | 2/2013 |
| WO | 2014033543 A2 | 3/2014 |
| WO | 2014033543 A3 | 6/2014 |

OTHER PUBLICATIONS

Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.

Apple D.J., et al., "Anterior Chamber Lenses Part 1: Complications and Pathology and a Review of Designs," Journal of Cataract Refractive Surgery, Mar. 1987, vol. 13 (2), pp. 157-174.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.

Atchinson D.A., "Optical Design of Intraocular Lenses. I. On-Axis Performance," American Academy of Optometry, 1989, vol. 66 (8), pp. 492-506.

Baikoff G., et al., "Angle-fixated Anterior Chamber Phakic Intraocular Lens for Myopia 7 to—Diopters," Journal of Refractive Surgery, May-Jun. 1998, vol. 14 (3), pp. 282-292.

Canovas C., et al., "Hybrid Adaptive-Optics Visual Simulator," Optical Letters, Jan. 15, 2010, vol. 35 (2), pp. 196-198.

Cheng X., et al., "Predicting Subjective Judgment of Best Focus with Objective Image Quality Metrics," Journal of Vision, Apr. 2004, vol. 4 (4), pp. 310-321.

CILCO Advertisement Brochure, Oct. 1982, 3 pages.

Cohen A.L., "Practical Design of a Bifocal Hologram Contact Lens or Intraocular Lens," Applied Optics, Jul. 1, 1992, vol. 31 (19), pp. 3750-3754.

(56) References Cited

OTHER PUBLICATIONS

De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.

Liou H.L., et al., "Anatomically Accurate, Finite Model Eye for Optical Modeling," Journal of Optical Society of America, Aug. 1997, vol. 14 (8), pp. 1684-1695.

Liou H.L., et al., "The Prediction of Spherical Aberration with Schematic Eyes," Ophthalmic and Physiological Optics, Jan. 1996, vol. 16 (4), pp. 348-354.

Marinho A., "Results are Encouraging for Phakic IOLs, but More Work is needed," Refractive Surgery, Feb. 2000, p. 12, 15.

Marsack J.D., et al., "Metrics of Optical Quality Derived from Wave Aberrations Predict Visual Performance," Journal of Vision, Apr. 2004, vol. 4 (4), pp. 322-328.

Menapace R., "The Capsular Tension Rings," Journal of Cataract & Refractive Surgery, Dec. 10, 2008, Chap. 3, pp. 27-44.

Monsoriu J.A., et al., "Devil's Lenses," Optics Express, Oct. 17, 2007, vol. 15 (21), pp. 13858-13864.

Morlock, R., et al., "Patient-Reported Spectacle Independence Questionnaire (PRSIQ): Development and Validation, "American Journal of Ophthalmology, Jun. 2017, vol. 178, pp. 101-114.

Navarro R., et al., "Accommodation-Dependent Model of the Human Eye with Aspherics," Journal of the Optical Society of America, Aug. 1985, vol. 2 (8), pp. 1273-1281.

Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.

Norrby S., et al., "Model Eyes for Evaluation of Intraocular Lenses," Applied Optics, Sep. 7, 2007, vol. 46 (26), pp. 6595-6605.

Olsen T., "Simple Method to Calculate the Surgically Induced Refractive Change," Journal of Cataract & Refractive Surgery, Mar. 1993, vol. 19 (2), pp. 319-320.

Packer M., et al., "Prospective Randomized Trial of an Anterior Surface Modified Prolate Intraocular Lens," Journal of Refractive Surgery. 2002, vol. 18 (6), pp. 692-696.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Praeger D.L., "Praeger Technique for the Insertion of the Copeland Radial IOL Posterior Chamber Placement," Copeland Lens, 1982, 7 pages.

Siedlecki D., et al., "Radial Gradient index Intraocular Lens: a Theoretical Model," Journal of Modern Optics, Feb. 10-Mar. 2008, vol. 55 (4-5), pp. 639-647.

Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Vass C., et al., "Prediction of Pseudophakic Capsular bag Diameter based on Biometric Variables," Journal of Cataract and Refractive Surgery, Oct. 1999, vol. 25 (10), pp. 1376-1381.

Venter, J.A., et al., "Visual Outcomes and Patient Satisfaction with a Rotational Asymmetric Refractive Intraocular Lens for Emmetropic Presbyopia," Cataract & Refractive Surgery, Mar. 2015, vol. 41 (3), pp. 585-593.

Villegas E.A., et al., "Correlation between Optical and Psychophy, Sical Parameters as a Function of Defocus," Optometry and Vision Science, Jan. 1, 2002, vol. 79 (1), pp. 60-67.

Wolffsohn J.S., et al., "Visual Function in Patient's Implanted with a Non-Concentric Multifocal Intraocular Lens," 2010.

Zemax, Optical Design Program User's Guide, Nov. 1, 2004, Part 1 of 2 and Chapter 1-11, Retrieved from the Internet: URL: www.itsabook.com.

\* cited by examiner

MULTI-REGION REFRACTIVE LENSES FOR VISION TREATMENT

CROSS REFERENCE TO RELATED APPLICATIONS

This application claims priority to U.S. Provisional Patent Application No. 62/955,327, filed on Dec. 30, 2019, the entire contents of which are hereby incorporated by reference.

BACKGROUND

Embodiments of the present disclosure relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL."

Monofocal IOLs are intended to provide vision correction at one distance only, usually the far focus. At the very least, since a monofocal IOL provides vision treatment at only one distance and since the typical correction is for far distance, spectacles are usually needed for good vision at near distances and sometimes for good vision at intermediate distances. The term "near vision" generally corresponds to vision provided when objects are at a distance from the subject eye at equal; or less than 1.5 feet. The term "distant vision" generally corresponds to vision provided when objects are at a distance of at least ab out 5-6 feet or greater. The term "intermediate vision" corresponds to vision provided when objects are at a distance of about 1.5 feet to about 5-6 feet from the subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near (add) power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Multifocal IOLs may also rely on a refractive optical surface to direct portions of light energy toward differing focal distances, thereby allowing the patient to clearly see both near and far objects. Such refractive optical surfaces may include multiple regions having differing optical powers, to direct the light energy towards the different focal distances as desired. Such refractive optics, however, may result in reduced distant vision quality.

It would be desirable to provide improved refractive IOL systems and methods that confer enhanced image quality at a variety of different focal distances, including for distant vision, as well as for an extended depth of focus optic or a full range optic. Embodiments of the present disclosure provide solutions that address the problems described above, and hence provide answers to at least some of these outstanding needs.

BRIEF SUMMARY

Embodiments herein described include ophthalmic lenses with an optic disposed about an optical axis having a refractive profile including a region having an add power and a first distance region and a second distance region extending outward from the first distance region which is vertex matched with the first distance region. The region having the add power may be a near region. The first distance region may be a central region of the optic that the optical axis extends through. The second distance region may have a lesser power than the first distance region in an amount of between −0.1 diopter and −0.5 diopter, inclusive. The add power may be between 1 diopter and 5 diopter, inclusive.

In addition, the region having the add power may be positioned between the first distance region and the second distance region and may also be adjacent both the first distance region and the second distance region. The first distance region and the second distance region may both extend outward from the region having the add power. The region having the add power may be a central region of the optic that the optical axis extends through.

The difference in power between the first distance region and the second distance region in any of the embodiments may be less than the add power. And, the second distance region may gradually decrease in power outward from the region having the add power. It is also envisioned that the region having the add power may have at least two different add powers.

The ophthalmic lens of any embodiment herein may also have a second region having an add power extending outward from the second distance region. Such a lens may have a third distance region extending outward from the second region having the add power, the third distance region being vertex matched with the second distance region and with the first distance region. In addition, the second distance region may gradually decrease in power towards the third distance region and the third distance region may gradually decrease in power outward from the second region having the add power.

It is envisioned that any embodiment herein may function as an extended depth of focus optic or a multifocal optic.

Embodiments herein described include a method comprising fabricating an optic for an ophthalmic lens, the optic being disposed about an optical axis and having a refractive profile including a region having an add power and a first distance region and a second distance region extending outward from the first distance region and being vertex matched with the first distance region.

The method may further comprise receiving an ophthalmic lens prescription, and fabricating the optic based on the ophthalmic lens prescription with the refractive profile based on the ophthalmic lens prescription. A vertex shift of the second distance region caused by the region having the add power may then be determined, and then based on the determined vertex shift, the first distance region and the second distance region may be vertex matched. This method of fabrication may be used to fabricate any lens disclosed herein.

Embodiments herein described include a system for fabricating an ophthalmic lens, the system including a processor configured to determine a refractive profile of an optic, the refractive profile including a region having an add power and a first distance region and a second distance region extending outward from the first distance region and being vertex matched with the first distance region. The system may include a manufacturing assembly that fabricates the optic based on the refractive profile.

The system may further comprise of an input for receiving an ophthalmic lens prescription, wherein the processor is configured to determine the refractive profile of the optic based on the ophthalmic lens prescription. The processor may also be configured to determine a vertex shift of the second distance region caused by the region having the add power, and may be configured to determine the refractive profile such that the first distance region and the second distance region are vertex matched based on the determined vertex shift. This system for fabricating may be used to fabricate any lens disclosed herein.

DETAILED DESCRIPTION

Figure 1:
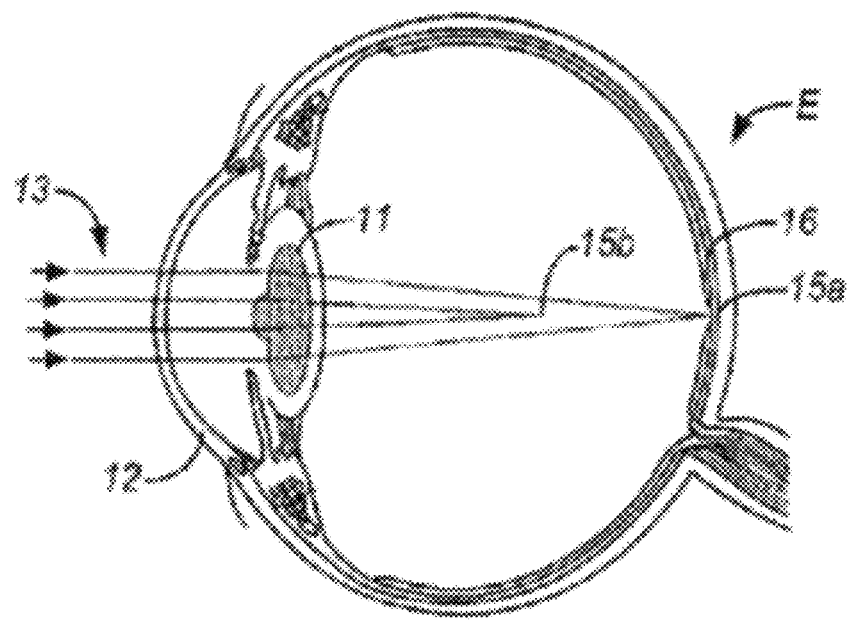
FIG. 1 illustrates a cross-sectional view of an eye with an implanted multifocal refractive intraocular lens.

FIG. 1 illustrates multifocal IOL lens geometries, aspects of which are described in U.S. Patent Publication No. 2011-0149236 A1, which is hereby incorporated by reference in its entirety.

FIG. 1 is a cross-sectional view of an eye E fit with a multifocal IOL 11. As shown, multifocal IOL 11 may, for example, comprise a bifocal IOL. Multifocal IOL 11 receives light 13 from at least a portion of cornea 12 at the front of eye E and is generally centered about the optical axis of eye E. For ease of reference and clarity, FIG. 1 does not disclose the refractive properties of other parts of the eye, such as the corneal surfaces. Only the refractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. As shown in FIG. 1, as light 13 enters from the front of the eye, the multifocal lens 11 directs the light 13 to form a far field focus 15a on the retina 16 for viewing distant objects and a near field focus 15b for viewing objects close to the eye. Depending on the distance from the source of light 13, the focus on retina 16 may be the near field focus 15b instead.

Figure 2:
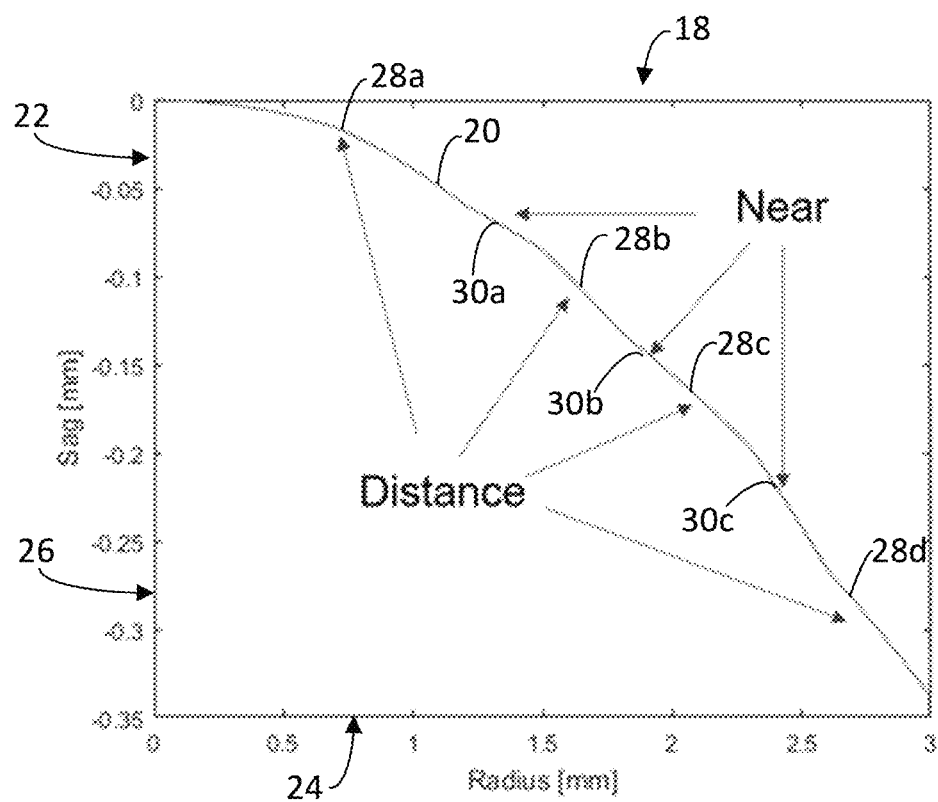
FIG. 2 illustrates a graph of a refractive profile of an anterior surface of an optic.

FIG. 2, for example, illustrates a graph of a refractive profile 18 of an anterior surface 20 of an optic. The optic may be implanted in a patient's eye similarly as the multifocal lens 11 shown in FIG. 1. The optic is disposed about an optical axis 22, and extends outward from the optical axis 22. The radius of the refractive profile 18 from the optical axis 22 is shown on the X-axis 24 in units of millimeters. The profile height of the refractive profile 18 is shown on the Y-axis 26 in units of millimeters.

The refractive profile 18 may be configured to correct ocular aberrations of the eye E, including ocular spherical aberrations, among others. The refractive profile 18 may be multifocal, including a bifocal design as shown in FIG. 2, and may include regions 28a-d that correspond to distant vision (or distance regions) and regions 30a-c that correspond to near vision (or near regions). The curvature of the distance regions 28a-d may be different than the curvature of the near regions 30a-c to provide for differing focal lengths of the respective regions. At least two focuses may be provided, such as the focuses 15a and 15b shown in FIG. 1, with the distance regions 28a-d corresponding to the far field focus 15a and the near regions 30a-c corresponding to the near field focus 15b. The refractive profile 18 may be circularly symmetrical around the optical axis 22, such that the regions 28a-d, 30a-c form annular regions around the optical axis 22.

As shown in FIG. 2, the regions 28a-d, 30a-c may be interwoven, with each of the plurality of near regions 30a-c positioned between and adjacent to respective distance regions 28a-d. Other configurations may be utilized. For example, the entirety of the near region may be positioned in a central region of the optic, aspheric designs may be utilized with gradual transitions between the peak power of the near regions and the distance regions, trapezoidal designs may be utilized with gradual transitions between the peak power of the near regions and the distance regions, and asymmetric designs may be utilized in which a split between near and distance zones depends on the angular coordinate.

The distance regions 28a-d have an add power of zero diopters (or no add power). The near regions 30a-c, however, each have an add power. The add power can comprise a variety of powers, including between 4 diopters and 1 diopter, inclusive (e.g., 4 diopter, 3 diopter, 2 diopter, 1.5 diopter, etc.), among other greater or lower powers. The near regions 30a-c may have a higher curvature and a generally higher overall power suitable for viewing at near distances. In an embodiment in which the optic is multifocal and has a greater number of focuses than two, then certain of the near regions 30a-c may have a different add power than each other to provide one or more additional focuses. As such, the add power used in different regions of the optic may be different.

Figure 3:
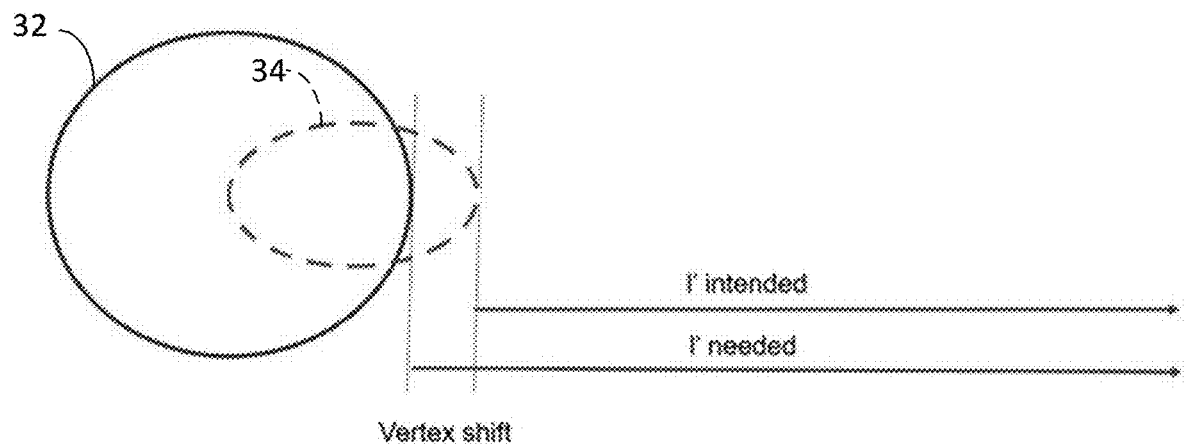
FIG. 3 illustrates a representation of an example of vertex shift.

An issue that may arise with an optic configured similarly as the optic shown in FIG. 2 is the principle of vertex shift. FIG. 3 for example illustrates a representation of an example of vertex shift. A representation of an optic is shown including a surface curvature 32 (shown in solid lines) configured for distant vision and a surface curvature 34 (shown in dashed lines) that is greater than the surface curvature 32 and is configured for near vision. Due to the greater curvature of the surface curvature 34, the vertex of the surface curvature 32 is actually shifted, resulting in a longer image distance needed to reach the retina than if the surface curvature 34 had not been present (I' needed compared to I' intended as marked in FIG. 3). As such, a modification of the surface curvature 32 to provide lesser power is desired.

Thus, referring back to FIG. 2, if a centermost distance region 28a has an add power of zero diopter (or no add power), then any subsequent distance region (for example region 28b) extending outward from a region having an add power (such as region 30a) will have its vertex shifted relative to the centermost distance region 28a. The subsequent distance region (for example region 28b) extending outward from the distance region 28a thus may be provided with a lesser power than the distance region 28a to vertex match with the centermost distance region 28a. The vertex shifting principle described in regard to FIG. 3 may be compounded if there are multiple near regions, as shown in FIG. 2 for example. As such, the additional distance regions (regions 28c, 28d) extending outward from the distance regions 28a, 28b and near regions 30b, 30c may be provided with a lesser power than the distance regions 28a, 28b to vertex match with the distance regions 28a, 28b.

Figure 4A:
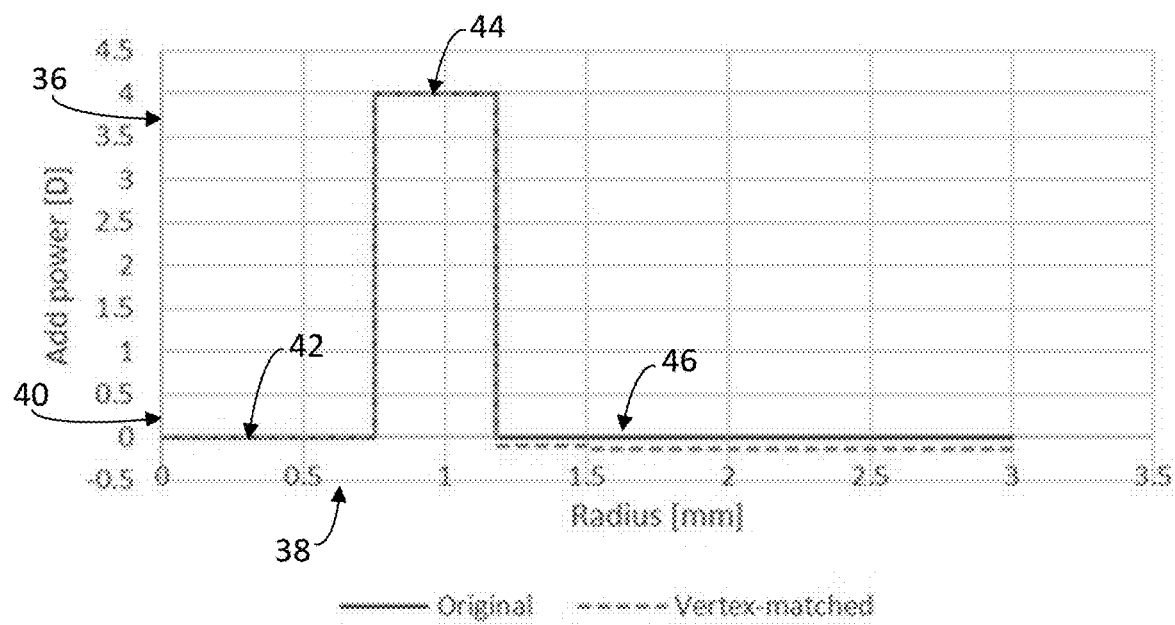
FIG. 4A illustrates an embodiment of an optic including vertex matched distance regions.

FIG. 4A illustrates an embodiment of an optic including vertex matched distance regions. FIG. 4A illustrates a graph of optical power of an optic having a refractive profile. The optic may be implanted in a patient's eye similarly as the multifocal lens 11 shown in FIG. 1. The optic is disposed about an optical axis 36, and has a refractive profile that extends outward from the optical axis 36. The radius of the refractive profile of the optic from the optical axis 36 is shown on the X-axis 38 in units of millimeters. The optical power of the refractive profile is shown on the Y-axis 40 in units of diopters.

The refractive profile reflected in FIG. 4A may be configured to correct ocular aberrations of the eye E, including ocular spherical aberrations, among others. The refractive profile reflected in FIG. 4A is a multifocal and bifocal design.

The refractive profile reflected in FIG. 4A may include a distance region 42. The distance region 42 may be positioned in a central region of the optic that the optical axis 36 extends through. The distance region 42 may have an add power of zero diopter (or no add power) and may be configured for distant vision. The distance region 42 may extend outward from the optical axis 36 to a radius of about 7.5 millimeters as shown in FIG. 4A, although other distances may be utilized as desired.

A region 44 having an add power may extend outward from the distance region 42. The region 44 may be adjacent to the distance region 42. The region 44 may have a greater surface curvature than the distance region 42 to provide for the add power. The region 44 may comprise a near region, configured for near vision, or may comprise an intermediate region for intermediate vision. The region 44 may have an add power of four diopters as shown in FIG. 4A, or may have another add power, such as a range between 5 diopters and 1 diopter, inclusive (e.g., 5 diopter, 4 diopter, 3 diopter, 2 diopter, 1.5 diopter, etc.), among other greater or lower powers. The region 44 may extend for about 0.5 millimeters as shown in FIG. 4A, although other radial distances (greater or lesser) may be provided as desired. The presence of the region 44 accordingly may vertex shift a distance region 46 that extends outward from the region 44.

A distance region 46 may be provided that extends outward from the distance region 42 and extends outward from the region 44. The region 44 may be positioned between the distance region 42 and the distance region 46 and adjacent to the distance regions 42, 46. The distance region 46 may extend outward from the region 44 to an outer periphery of the optic or to another radial distance. The distance region 46 may extend for a radial distance of about 1.8 millimeters (to provide an optic extending to an outer periphery of 3 millimeters), although other radial distances may be provided as well as other sizes of optics. The refractive profile represented in FIG. 4A may be circularly symmetrical around the optical axis 36, such that the regions 42, 44, 46 form annular regions around the optical axis 36. The distance region 42 may be positioned in a central region of the optic, the distance region 46 may be positioned in a peripheral region of the optic, and the region 44 may be positioned in an intermediate region of the optic.

The distance region 46 may have its vertex shifted by the presence of region 44. To compensate, the distance region 46 may be configured to have a lesser power than the central distance region 42. The distance region 46 may be vertex matched with the distance region 42. The dashed line shown in FIG. 4A represents the lesser power of the distance region 46 than the central distance region 42. The distance region 46 may have its power reduced by an amount to vertex match with the distance region 42. The lesser power of the distance region 46 may be between −0.1 diopter and −0.5 diopter (e.g., −0.1 diopter, −0.15 diopter, −0.2 diopter, −0.3 diopter, −0.4 diopter, or −0.5 diopter, etc.) among other greater or lower powers. The power of the distance region 46 may be reduced by an amount that is less than the increase in power of the region 44 from the central distance region 42.

The distance region 46 may gradually decrease in power outward from the region 44. As shown in FIG. 4A, the distance region 46 at the transition between the region 44 and the distance region 46 may have its power reduced by about −0.1 diopter, which may gradually decrease to about −0.2 diopter at the outer periphery of the distance region 46. The amount of gradual reduction may be varied as desired.

At least two focuses may be provided with the embodiment shown in FIG. 4A, such as the focuses 15a and 15b shown in FIG. 1, with the distance regions 42, 46 corresponding to the far field focus 15a and the region 44 having the add power corresponding to the near field focus 15b.

Figure 4B:
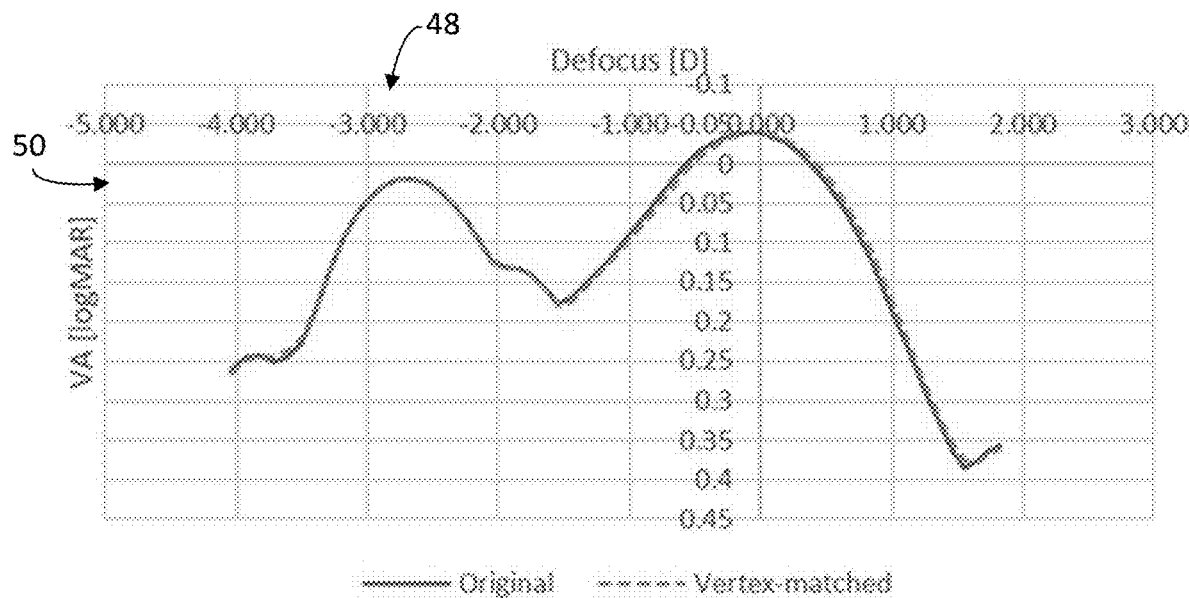
FIG. 4B illustrates a graph of a representation of visual acuity, for a 3 millimeter pupil diameter.

FIG. 4B illustrates a graph of a representation of visual acuity for the embodiment shown in FIG. 4A, for a 3 millimeter pupil diameter. Defocus in units of diopter is shown on the X-axis 48 and visual acuity shown as the logarithm of the minimum angle of resolution is shown on the Y-axis 50. The through focus visual acuity is shown to be similar at a 3 millimeter pupil diameter for a vertex matched and non-vertex matched optic of FIG. 4A.

Figure 4C:
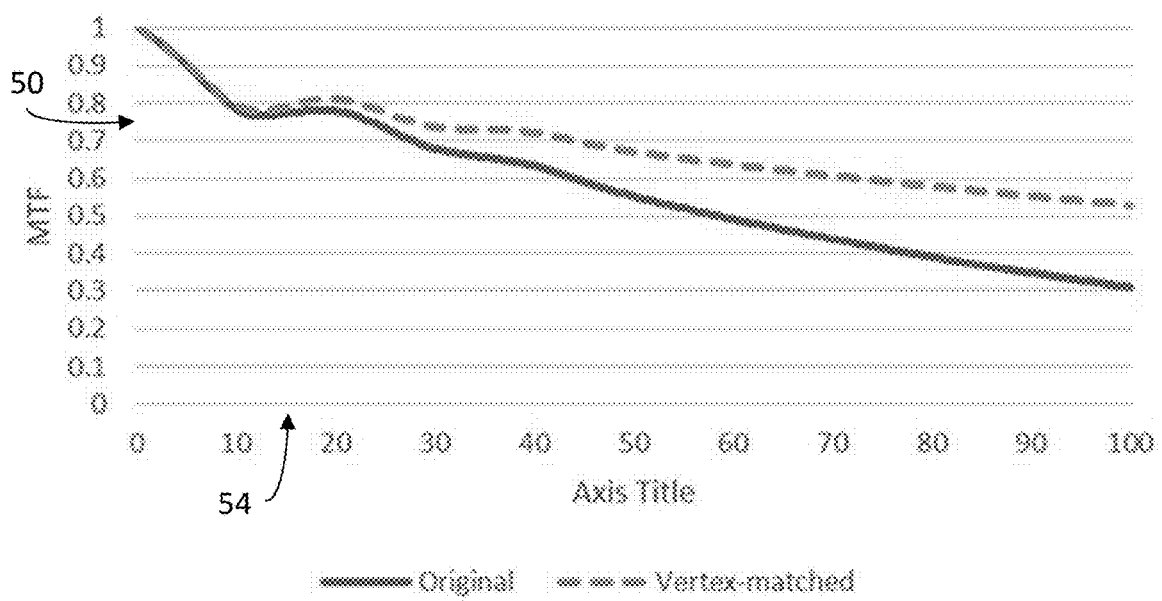
FIG. 4C illustrates a graph of a representation of modulation transfer function (MTF) for a 5 millimeter pupil diameter.

FIG. 4C, however, illustrates a graph of a representation of modulation transfer function (MTF) for the embodiment shown in FIG. 4A, for a 5 millimeter pupil diameter. The MTF is shown on the Y-axis 52 and frequency in units of [cycles/millimeters] is shown on the X-axis 54. The MTF for the vertex matched embodiment of FIG. 4A (shown in dashed lines in FIG. 4C) is shown to be improved relative to an embodiment of FIG. 4A in which the distance region 46 is not vertex matched (represented in solid line in FIG. 4C).

Figure 4D:
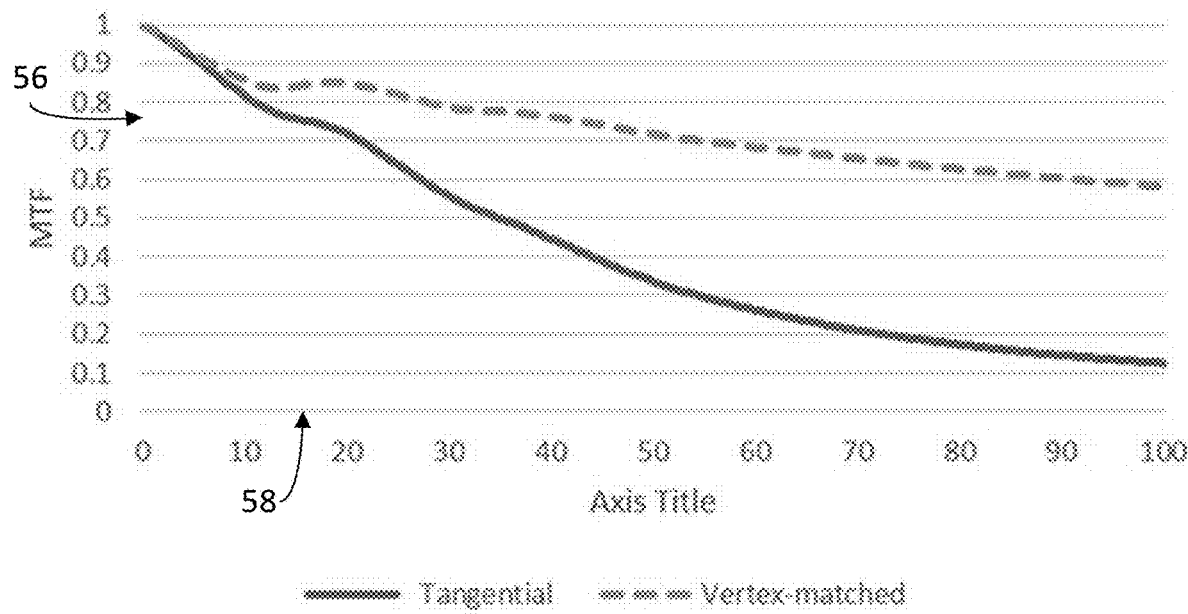
FIG. 4D illustrates a illustrates a graph of a representation of modulation transfer function (MTF), for a 6 millimeter pupil diameter.

FIG. 4D illustrates a illustrates a graph of a representation of modulation transfer function (MTF) for the embodiment shown in FIG. 4A, for a 6 millimeter pupil diameter. The MTF is shown on the Y-axis 56 and [cycles/millimeters] is shown on the X-axis 58. The MTF for the vertex matched embodiment of FIG. 4A (shown in dashed lines in FIG. 4D) is shown to be improved relative to an embodiment of FIG. 4A in which the distance region 46 is not vertex matched (represented in solid line in FIG. 4D). The improvement in MTF is greater for a larger pupil diameter (6 millimeter as shown in FIG. 4D) than for a smaller pupil diameter (5 millimeter as shown in FIG. 4C).

Figure 5A:
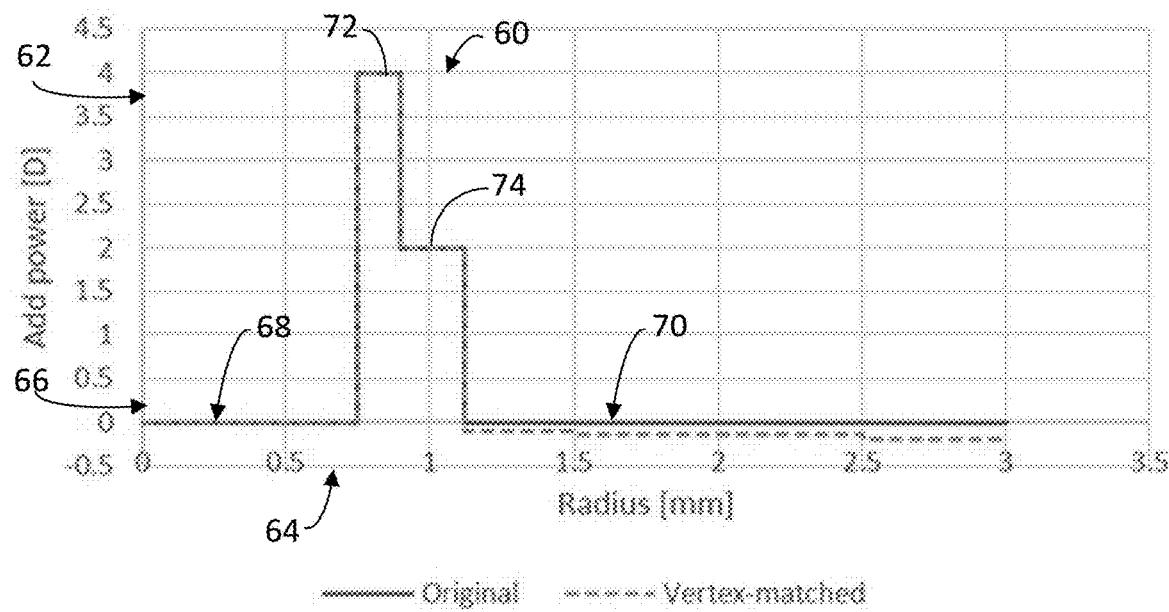
FIG. 5A illustrates an embodiment of an optic including vertex matched distance regions.

FIG. 5A illustrates an embodiment of an optic including vertex matched distance regions. FIG. 5A illustrates a graph of optical power of an optic having a refractive profile. The optic shown in FIG. 5A differs from the embodiment shown in FIG. 4A in that the region 60 having the add power has two different add powers (rather than a single add power of the region 44 shown in FIG. 4A). The optic may be implanted in a patient's eye similarly as the multifocal lens 11 shown in FIG. 1. The optic is disposed about an optical axis 62, and has a refractive profile that extends outward from the optical axis 62. The radius of the refractive profile of the optic from the optical axis 62 is shown on the X-axis 64 in units of millimeters. The optical power of the refractive profile is shown on the Y-axis 66 in units of diopters.

The refractive profile reflected in FIG. 5A may be configured to correct ocular aberrations of the eye E, including ocular spherical aberrations, among others. The refractive profile reflected in FIG. 5A is an extended depth of focus design.

The refractive profile reflected in FIG. 5A may include a distance region 68, which is similar to the distance region 42 shown in FIG. 4A. The distance region 68 may be positioned in a central region of the optic that the optical axis 62 extends through. The distance region 68 may have an add power of zero diopter (or no add power) and may be configured for distant vision. The distance region 68 may extend outward from the optical axis 62 to a radius of about 7.5 millimeters as shown in FIG. 5A, although other distances may be utilized as desired.

A region 60 having two different add powers may extend outward from the distance region 68. The region 60 may be adjacent to the distance region 68. The region 60 may have two different surface curvatures, each having a greater surface curvature than the distance region 68 to provide for the add power. The portion 72 of the region 60 having a greater add power may comprise a near region, configured for near vision, and the portion 74 of the region 60 having an add power less than the portion 72 may comprise an intermediate region for intermediate vision. Other designations of near and intermediate focus may be provided for the portions 72, 74 of the region 60 as desired.

The region 60 may include a centermost portion 72 that has an add power of four diopters as shown in FIG. 5A, or may have another add power, such as a range between 5 diopters and 1 diopter, inclusive (e.g., 5 diopter, 4 diopter, 3 diopter, 2 diopter, 1.5 diopter, etc.), among other greater or lower powers. The portion 72 of the region 60 may extend for about 0.2 millimeters as shown in FIG. 5A, although other radial distances (greater or lesser) may be provided as desired.

The region 60 may include an adjacent outermost portion 74 that has a lesser add power than the centermost portion 72 and extends outward from the portion 72. The adjacent outermost portion 74 may have an add power of two diopters as shown in FIG. 5A, or may have another add power, such as a range between 5 diopters and 1 diopter, inclusive (e.g., 5 diopter, 4 diopter, 3 diopter, 2 diopter, 1.5 diopter, etc.), among other greater or lower powers. The adjacent outermost portion 74 accordingly may have a greater add power than the portion 72. The portion 74 of the region 60 may extend for about 0.3 millimeters as shown in FIG. 5A, although other radial distances (greater or lesser) may be provided as desired.

In other embodiments, the add powers of the portions 72, 74 may be alternated such that the portion 72 has a lesser add power than the portion 74. In addition, the add powers of the portions 72, 74 may be varied.

A distance region 70 may be provided that extends outward from the distance region 68 and extends outward from the region 60. The region 60 may be positioned between the distance region 68 and the distance region 70 and adjacent to the distance regions 68, 70. The distance region 70 may extend outward from the region 60 to an outer periphery of the optic or to another radial distance. The distance region 70 may extend for a radial distance of about 1.8 millimeters (to provide an optic extending to an outer periphery of 3 millimeters), although other radial distances may be provided as well as other sizes of optics. The refractive profile represented in FIG. 5A may be circularly symmetrical around the optical axis 62, such that the regions 68, 60, 70 form annular regions around the optical axis 62. The distance region 68 may be positioned in a central region of the optic, the distance region 70 may be positioned in a peripheral region of the optic, and the region 60 may be positioned in an intermediate region of the optic.

The distance region 70 may have its vertex shifted by the presence of region 60. To compensate, the distance region 70 may be configured to have a lesser power than the central distance region 68. The distance region 70 may be vertex matched with the distance region 68. The dashed line shown in FIG. 5A represents the lesser power of the distance region 70 than the central distance region 68. The distance region 70 may have its power reduced by an amount to vertex match with the distance region 68. The lesser power of the distance region 70 may be between −0.1 diopter and −0.5 diopter (e.g., −0.1 diopter, −0.15 diopter, −0.2 diopter, −0.3 diopter, −0.4 diopter, or −0.5 diopter, etc.) among other greater or lower powers. The power of the distance region 70 may be reduced by an amount that is less than the increase in power of the region 60 from the central distance region 68.

The distance region 70 may gradually decrease in power outward from the region 60. As shown in FIG. 5A, the distance region 70 at the transition between the region 60 and the distance region 70 may have its power reduced by about −0.1 diopter, which may gradually decrease to about −0.25 diopter at the outer periphery of the distance region 46. The amount of gradual reduction may be varied as desired.

An extended depth of focus may be provided with the embodiment shown in FIG. 5A. The distance regions 68, 70 may correspond to a far field focus and the portion 72 of the region 60 may correspond to a near field focus. The portion 74 of the region 60 may correspond to an intermediate focus.

Figure 5B:
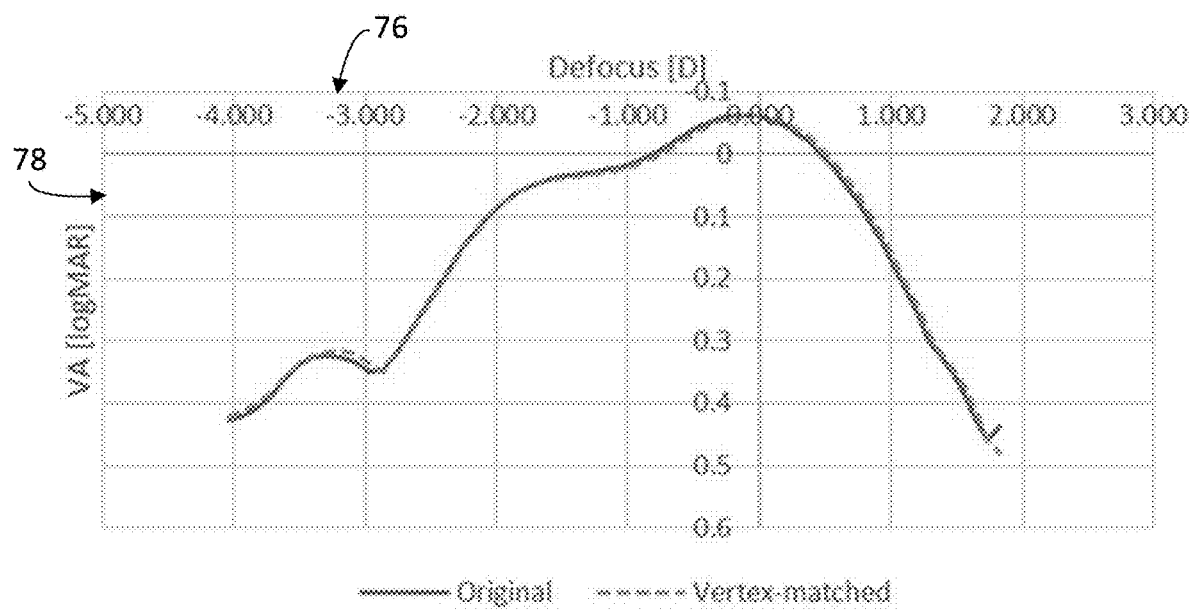
FIG. 5B illustrates a graph of a representation of visual acuity, for a 3 millimeter pupil diameter.

FIG. 5B illustrates a graph of a representation of visual acuity for the embodiment shown in FIG. 5A, for a 3 millimeter pupil diameter. Defocus in units of diopter is shown on the X-axis 76 and visual acuity shown as the logarithm of the minimum angle of resolution is shown on the Y-axis 78. The through focus visual acuity is shown to be similar at a 3 millimeter pupil diameter for a vertex matched and non-vertex matched optic of FIG. 5A.

Figure 5C:
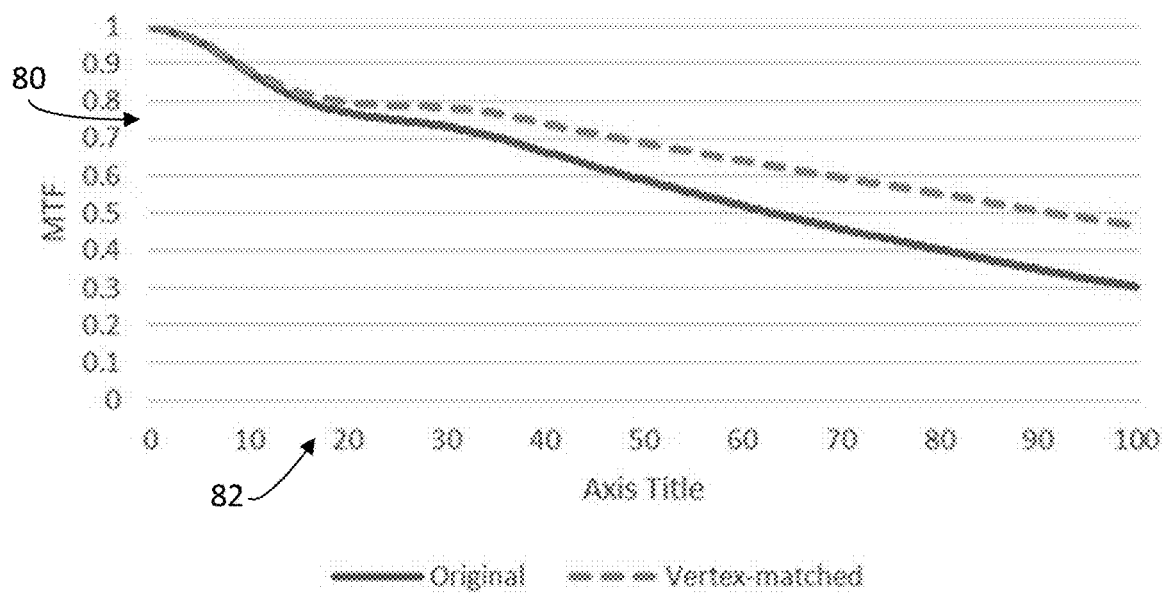
FIG. 5C illustrates a graph of a representation of modulation transfer function (MTF), for a 5 millimeter pupil diameter.

FIG. 5C, however, illustrates a graph of a representation of modulation transfer function (MTF) for the embodiment shown in FIG. 5A, for a 5 millimeter pupil diameter. The MTF is shown on the Y-axis 80 and frequency in units of [cycles/millimeters] is shown on the X-axis 82. The MTF for the vertex matched embodiment of FIG. 5A (shown in dashed lines in FIG. 5C) is shown to be improved relative to an embodiment of FIG. 5A in which the distance region 70 is not vertex matched (represented in solid line in FIG. 5C).

Figure 5D:
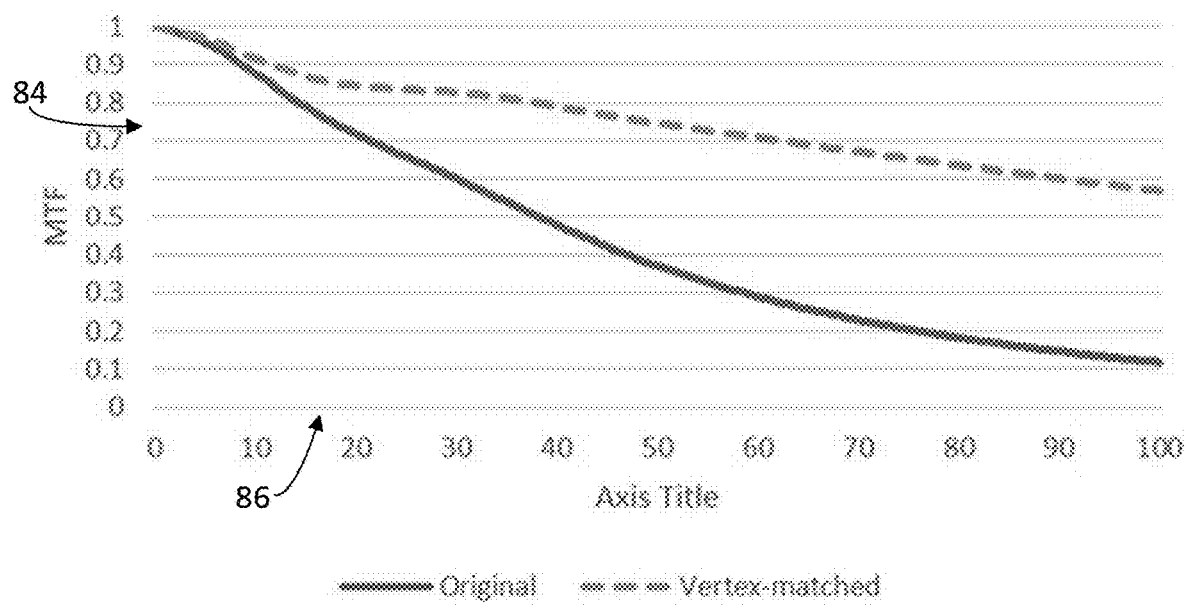
FIG. 5D illustrates a illustrates a graph of a representation of modulation transfer function, for a 6 millimeter pupil diameter.

FIG. 5D illustrates a illustrates a graph of a representation of modulation transfer function (MTF) for the embodiment shown in FIG. 5A, for a 6 millimeter pupil diameter. The MTF is shown on the Y-axis 84 and frequency in units of [cycles/millimeters] is shown on the X-axis 86. The MTF for the vertex matched embodiment of FIG. 5A (shown in dashed lines in FIG. 5D) is shown to be improved relative to an embodiment of FIG. 5A in which the distance region 70 is not vertex matched (represented in solid line in FIG. 5D). The improvement in MTF is greater for a larger pupil diameter (6 millimeter as shown in FIG. 5D) than a smaller pupil diameter (5 millimeter as shown in FIG. 5C).

Figure 6A:
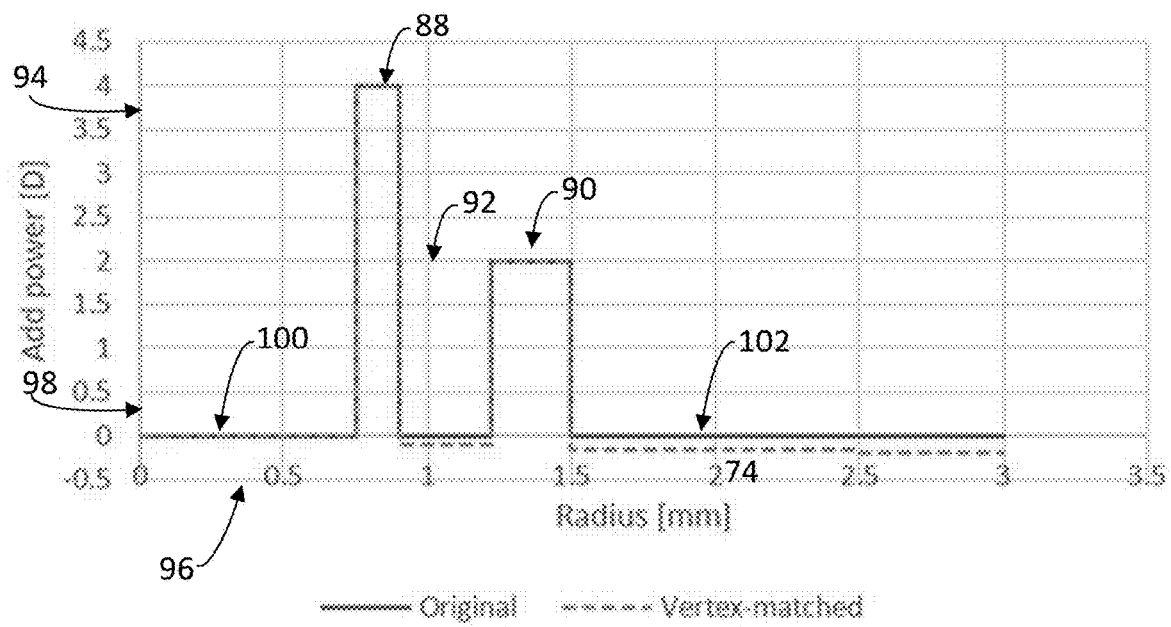
FIG. 6A illustrates an embodiment of an optic including vertex matched distance regions.

FIG. 6A illustrates an embodiment of an optic including vertex matched distance regions. FIG. 6A illustrates a graph of optical power of an optic having a refractive profile. The optic shown in FIG. 6A differs from the embodiment shown in FIG. 5A in that two regions 88, 90 are provided having two different add powers with a distance region 92 positioned between the two regions 88, 90 in the embodiment of FIG. 6A. The optic may be implanted in a patient's eye similarly as the multifocal lens 11 shown in FIG. 1. The optic is disposed about an optical axis 94, and has a refractive profile that extends outward from the optical axis 94. The radius of the refractive profile of the optic from the optical axis 94 is shown on the X-axis 96 in units of millimeters. The optical power of the refractive profile is shown on the Y-axis 98 in units of diopters.

The refractive profile reflected in FIG. 6A may be configured to correct ocular aberrations of the eye E, including ocular spherical aberrations, among others. The refractive profile reflected in FIG. 6A is an extended depth of focus design (with the region 88 directing light to a focus, and the region 90 directing light to a different focus, and a far focus being provided by the distance regions 100, 92, 102).

The refractive profile reflected in FIG. 6A may include a distance region 100, which is similar to the distance region 42 shown in FIG. 4A and the distance region 68 shown in FIG. 5A. The distance region 100 may be positioned in a central region of the optic that the optical axis 94 extends through. The distance region 100 may have an add power of zero diopter (or no add power) and may be configured for distant vision. The distance region 100 may extend outward from the optical axis 94 to a radius of about 7.5 millimeters as shown in FIG. 6A, although other distances may be utilized as desired.

A region 88 having an add power may extend outward from the distance region 100. The region 88 may be adjacent to the distance region 100. The region 88 may have a greater surface curvature than the distance region 100 to provide for the add power. The region 88 may comprise a near region, configured for near vision, or may be configured as an intermediate region for intermediate vision. The region 88 may have an add power of four diopters as shown in FIG. 6A, or may have another add power, such as a range between 5 diopters and 1 diopter, inclusive (e.g, 5 diopter, 4 diopter, 3 diopter, 2 diopter, 1.5 diopter, etc.), among other greater or lower powers. The region 88 may extend for about 0.2 millimeters as shown in FIG. 6A, although other radial distances (greater or lesser) may be provided as desired.

A distance region 92 may be provided that extends outward from the distance region 100 and extends outward from the region 88. The region 88 may be positioned between the distance region 100 and the distance region 92 and adjacent to the distance regions 100, 92. The distance region 92 may extend outward from the region 88 for a distance of about 0.3 millimeters for a distance from the optical axis 94 of about 1.2 millimeters, although other distances may be provided.

The distance region 92 may have its vertex shifted by the presence of region 88. To compensate, the distance region 92 may be configured to have a lesser power than the central distance region 100. The distance region 92 may be vertex matched with the distance region 100. The dashed line shown in FIG. 6A represents the lesser power of the distance region 92 than the central distance region 100. The distance region 92 may have its power reduced by an amount to vertex match with the distance region 100. The lesser power of the distance region 92 may be between −0.1 diopter and −0.5 diopter (e.g., −0.1 diopter, −0.15 diopter, −0.2 diopter, −0.3 diopter, −0.4 diopter, or −0.5 diopter, etc.) among other greater or lower powers. The power of the distance region 92 may be reduced by an amount that is less than the increase in power of the region 88 from the central distance region 100.

The distance region 92 may gradually decrease in power outward from the region 88. As shown in FIG. 6A, the distance region 92 at the transition between the region 88 and the distance region 92 may have its power reduced by about −0.1 diopter, which may gradually decrease to about −0.15 diopter at the outer periphery of the distance region 92. The amount of gradual reduction may be varied as desired.

A region 90 having an add power may extend outward from the distance regions 100, 92 and the region 88. The region 90 may be adjacent to the distance region 92. The region 90 may have a greater surface curvature than the distance region 92, to provide for the add power. The region 90 may comprise an intermediate region, configured for intermediate vision, or may be configured to have different add powers corresponding to different vision distances (such as near vision). The region 90 may have an add power of two diopters as shown in FIG. 6A, or may have another add power, such as a range between 5 diopters and 1 diopter, inclusive (e.g., 5 diopter, 4 diopter, 3 diopter, 2 diopter, 1.5 diopter, etc.), among other greater or lower powers. The region 90 may extend for about 0.3 millimeters as shown in FIG. 6A, although other radial distances (greater or lesser) may be provided as desired.

The region 90 may have a lesser add power than the centermost region 88 having an add power, to provide for a different focal length than the centermost region 88. In other embodiments, the add powers of the regions 90, 88 may be alternated such that the region 88 has a lesser add power than the region 90. In addition, the add powers of the regions 88, 90 may be varied.

A distance region 102 may be provided that extends outward from the distance regions 100, 92 and extends outward from the regions 88, 90. The region 90 may be positioned between the distance region 92 and the distance region 102 and adjacent to the distance regions 92, 102. The distance region 102 may extend outward from the region 90 for a distance of about 1.5 millimeters for a distance from the optical axis 94 of about 3 millimeters, although other distances may be provided.

The distance region 102 may have its vertex shifted by the presence of region 90. To compensate, the distance region 102 may be configured to have a lesser power than the central distance region 100 and the intermediate distance region 92. The distance region 102 may be vertex matched with both the central distance region 100 and the intermediate distance region 92. The dashed line shown in FIG. 6A represents the lesser power of the distance region 102 than the central distance region 100 and the intermediate distance region 92. The distance region 102 may have its power reduced by an amount to vertex match with the distance regions 100, 92. The lesser power of the distance region 102 may be between −0.1 diopter and −0.5 diopter (e.g., −0.1 diopter, −0.15 diopter, −0.2 diopter, −0.3 diopter, −0.4 diopter, or −0.5 diopter, etc.) among other greater or lower powers. The power of the distance region 102 may be reduced by an amount that is less than the increase in power of the region 90 from the intermediate distance region 92.

The distance region 102 may gradually decrease in power outward from the region 90. As shown in FIG. 6A, the distance region 102 at the transition between the region 90 and the distance region 102 may have its power reduced by about −0.15 diopter, which may gradually decrease to about −0.25 diopter at the outer periphery of the distance region 102. The amount of gradual reduction may be varied as desired.

The refractive profile represented in FIG. 6A may be circularly symmetrical around the optical axis 94, such that the regions 100, 88, 92, 90, 102 form annular regions around the optical axis 94.

Although the embodiment of FIG. 6A is shown with two regions 88, 90 having add powers, the number of add powers of these individual regions may be increased (to two or more each, as shown in FIG. 5A), and the total number of regions 88, 90 having add powers may be varied. For example, FIG. 6A shows two regions 88, 90 having add powers, although three or more may be provided, and may include intermediate distance portions therebetween, which may be vertex matched with each other.

An extended depth of focus may be provided with the embodiment shown in FIG. 6A. The distance regions 100, 92, 102 may correspond to a far field focus and the region 88 may correspond to a near field focus. The region 90 may correspond to an intermediate focus.

Figures 6B, 6C:
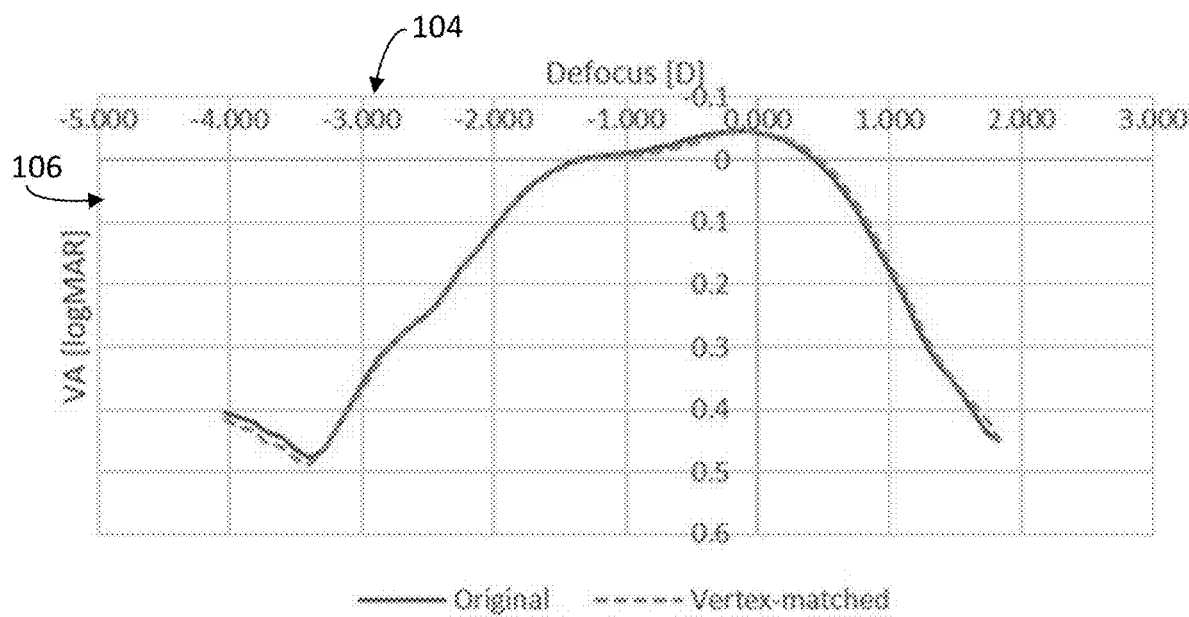
FIG. 6B illustrates a graph of a representation of visual acuity, for a 3 millimeter pupil diameter.
FIG. 6C illustrates a graph of a representation of modulation transfer function (MTF), for a 5 millimeter pupil diameter.

FIG. 6B illustrates a graph of a representation of visual acuity for the embodiment shown in FIG. 6A, for a 3 millimeter pupil diameter. Defocus in units of diopter is shown on the X-axis 104 and visual acuity shown as the logarithm of the minimum angle of resolution is shown on the Y-axis 106. The through focus visual acuity is shown to be similar at a 3 millimeter pupil diameter for a vertex matched and non-vertex matched optic of FIG. 6A.

FIG. 6C, however, illustrates a graph of a representation of modulation transfer function (MTF) for the embodiment shown in FIG. 6A, for a 5 millimeter pupil diameter. The MTF is shown on the Y-axis 108 and frequency in units of [cycles/millimeters] is shown on the X-axis 110. The MTF for the vertex matched embodiment of FIG. 6A (shown in dashed lines in FIG. 6C) is shown to be improved relative to an embodiment of FIG. 6A in which the distance regions 92, 102 are not vertex matched (represented in solid line in FIG. 6C).

Figure 6D:
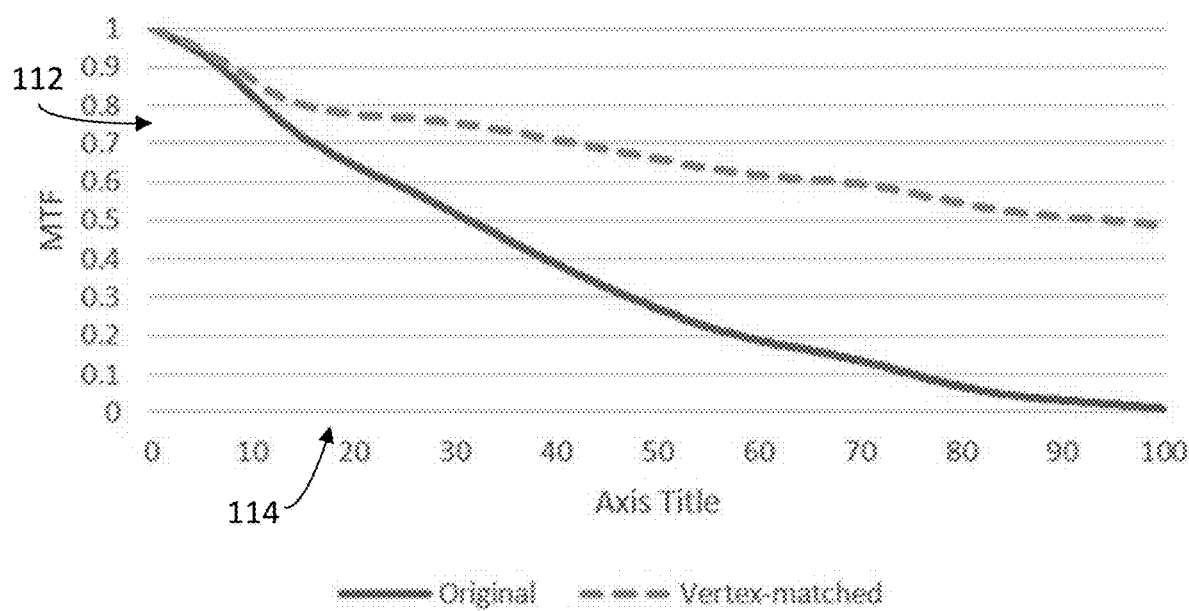
FIG. 6D illustrates a graph of a representation of modulation transfer function (MTF), for a 6 millimeter pupil diameter.

FIG. 6D illustrates a illustrates a graph of a representation of modulation transfer function (MTF) for the embodiment shown in FIG. 6A, for a 6 millimeter pupil diameter. The MTF is shown on the Y-axis 112 and frequency in units of [cycles/millimeters] is shown on the X-axis 114. The MTF for the vertex matched embodiment of FIG. 6A (shown in dashed lines in FIG. 6D) is shown to be improved relative to an embodiment of FIG. 6A in which the distance regions 92, 102 are not vertex matched (represented in solid line in FIG. 6D). The improvement in MTF is greater for a larger pupil diameter (6 millimeter as shown in FIG. 6D) than a smaller pupil diameter (5 millimeter as shown in FIG. 6C).

Figure 7A:
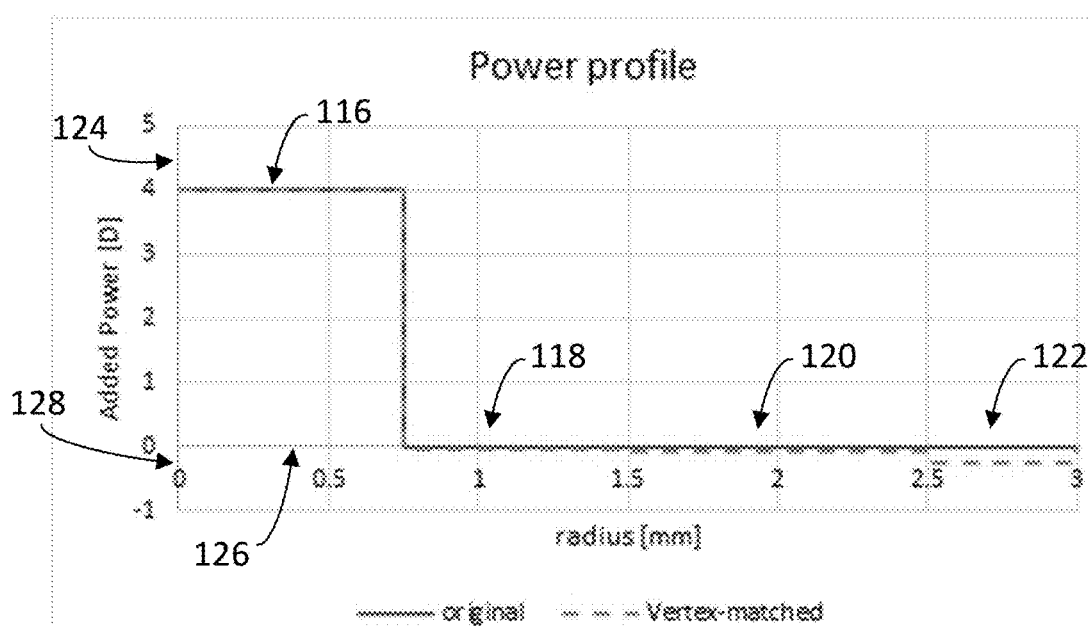
FIG. 7A illustrates an embodiment of an optic including vertex matched di stance regions.

FIG. 7A illustrates an embodiment of an optic including vertex matched distance regions. FIG. 7A illustrates a graph of optical power of an optic having a refractive profile. The optic shown in FIG. 7A differs from the embodiment shown in FIG. 5A in that the region 116 having the add power is positioned in a central region of the optic that the optical axis 124 extends through. A plurality of distance regions 118, 120, 122 (more clearly marked in FIG. 7B) each extend outward from the region 116 and are vertex matched with each other. The distance regions 118, 120, 122 are adjacent to each other and the distance region 118 is adjacent to the region 116. The optic may be implanted in a patient's eye similarly as the multifocal lens 11 shown in FIG. 1. The optic is disposed about an optical axis 124, and has a refractive profile that extends outward from the optical axis 124. The radius of the refractive profile of the optic from the optical axis 124 is shown on the X-axis 126 in units of millimeters. The optical power of the refractive profile is shown on the Y-axis 128 in units of diopters.

The refractive profile reflected in FIG. 7A may be configured to correct ocular aberrations of the eye E, including ocular spherical aberrations, among others. The refractive profile reflected in FIG. 7A is an extended depth of focus design.

A region 116 having an add power may comprise a near region, configured for near vision, or may be configured as an intermediate region for intermediate vision. The region 116 may have an add power of four diopters as shown in FIG. 7A, or may have another add power, such as a range between 5 diopters and 1 diopter, inclusive (e.g., 5 diopter, 4 diopter, 3 diopter, 2 diopter, 1.5 diopter, etc.), among other greater or lower powers. The region 116 may extend for about 0.7 millimeters as shown in FIG. 7A, although other radial distances (greater or lesser) may be provided as desired.

Figure 7B:
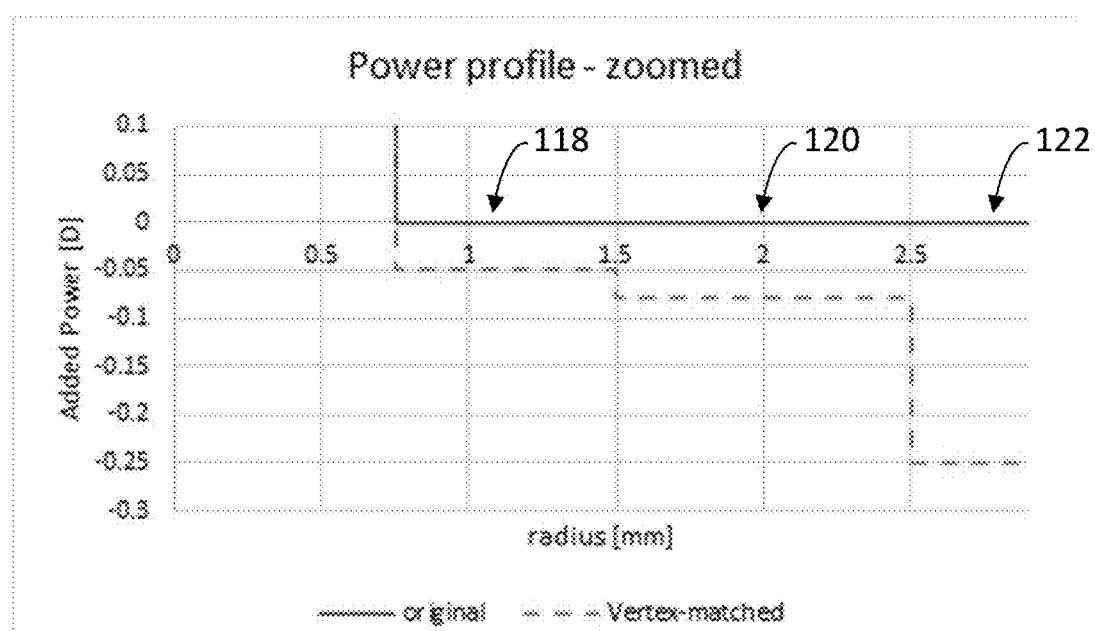
FIG. 7B illustrates a rescaled close-up view of FIG. 7A.

Referring to FIG. 7B, a first distance region 118 may be provided that extends outward from the region 116. A second distance region 120 extending from the first distance region 118 and a third distance region 122 extending from the second distance region 120 may be provided.

The distance regions 118, 120, 122 may have their vertices shifted by the presence of region 116. To compensate, the distance regions 118, 120, 122 may be configured to have a lesser power than the central region 116. The distance regions 118, 120, 122 may be vertex matched with each other. The dashed line shown in FIG. 7B represents the lesser power of the distance regions 118, 120, 122. The lesser power of the distance regions 118, 120, 122 may be between −0.1 diopter and −0.5 diopter (e.g., −0.1 diopter, −0.15 diopter, −0.2 diopter, −0.3 diopter, −0.4 diopter, or −0.5 diopter, etc.) among other greater or lower powers. The power of the distance regions 118, 120, 122 may be reduced by an amount that is less than the increase in power of the region 116.

The distance region 120 may gradually decrease in power outward from the distance region 118, and the distance region 122 may gradually decrease in power outward from the distance region 120. The amount of gradual reduction may be varied as desired.

The refractive profile represented in FIGS. 7A and 7B may be circularly symmetrical around the optical axis 124, such that the regions 116, 118, 120, 122 form annular regions around the optical axis 124.

Although the embodiment of FIGS. 7A and 7B is shown with one region 116 having an add power, the number of add powers of this region may be increased and the total number of regions having add powers may be varied.

An extended depth of focus may be provided with the embodiment shown in FIGS. 7A and 7B.

Figure 7C:
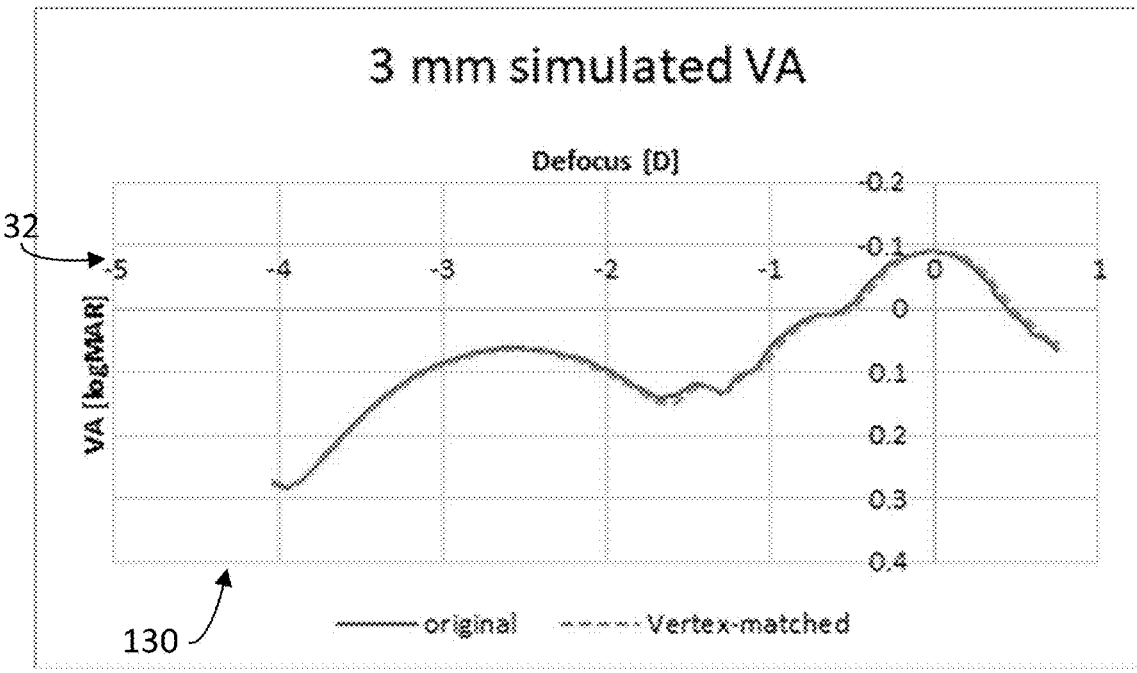
FIG. 7C illustrates a graph of a representation of visual acuity, for a 3 millimeter pupil diameter.

FIG. 7C illustrates a graph of a representation of visual acuity for the embodiment shown in FIGS. 7A and 7B, for a 3 millimeter pupil diameter. Defocus in units of diopter is shown on the X-axis 130 and visual acuity shown as the logarithm of the minimum angle of resolution is shown on the Y-axis 132. The through focus visual acuity is shown to be similar at a 3 millimeter pupil diameter for a vertex matched and non-vertex matched optic of FIG. 7C.

Figure 7D:
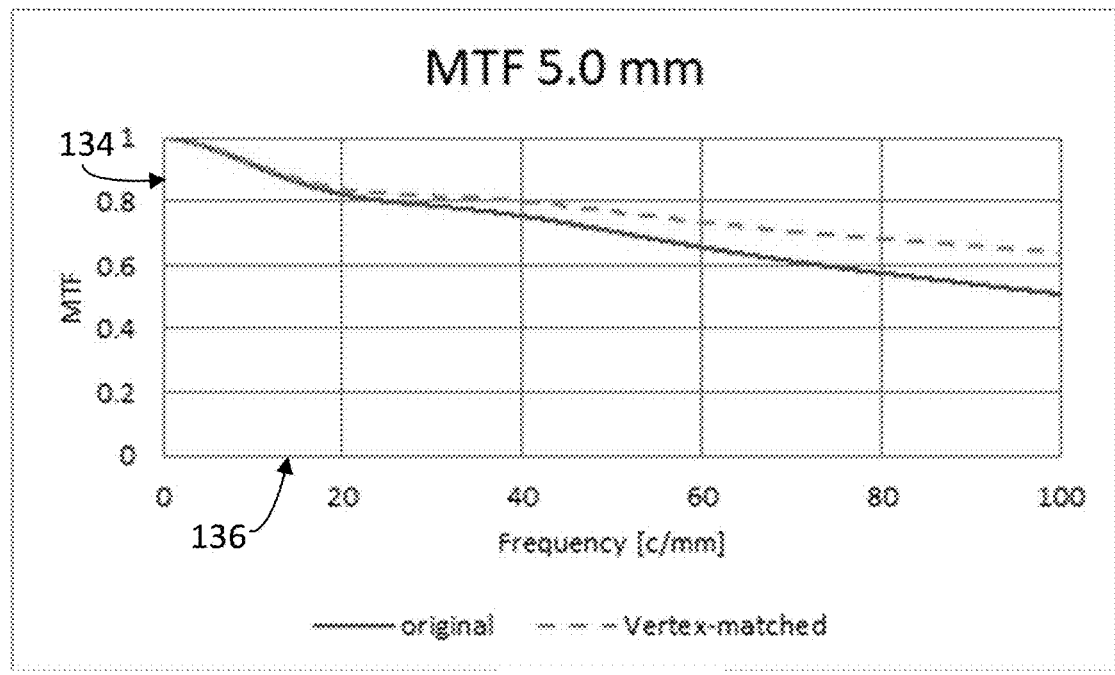
FIG. 7D illustrates a graph of a representation of modulation transfer function (MTF) for a 5 millimeter pupil diameter.

FIG. 7D, however, illustrates a graph of a representation of modulation transfer function (MTF) for the embodiment shown in FIGS. 7A and 7B, for a 5 millimeter pupil diameter. The MTF is shown on the Y-axis 134 and frequency in units of [cycles/millimeters] is shown on the X-axis 136. The MTF for the vertex matched embodiment of FIGS. 7A and 7B (shown in dashed lines in FIG. 7D) is shown to be improved relative to an embodiment in which the distance regions are not vertex matched (represented in solid line in FIG. 7D).

Figure 7E:
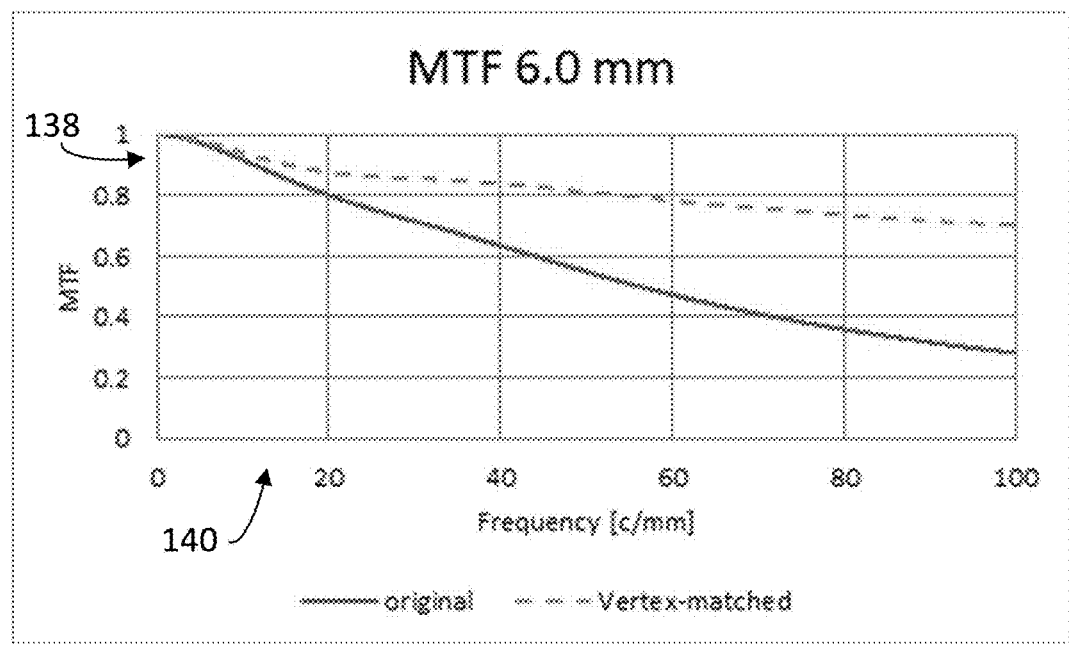
FIG. 7E illustrates a illustrates a graph of a representation of modulation transfer function (MTF), for a 6 millimeter pupil diameter.

FIG. 7E illustrates a illustrates a graph of a representation of modulation transfer function (MTF) for the embodiment shown in FIGS. 7A and 7B, for a 6 millimeter pupil diameter. The MTF is shown on the Y-axis 138 and frequency in units of [cycles/millimeters] is shown on the X-axis 140. The MTF for the vertex matched embodiment of FIGS. 7A and 7B (shown in dashed lines in FIG. 7E) is shown to be improved relative to an embodiment in which the distance regions are not vertex matched (represented in solid line in FIG. 7E). The improvement in MTF is greater for a larger pupil diameter (6 millimeter as shown in FIG. 7E) than a smaller pupil diameter (5 millimeter as shown in FIG. 7D).

An optic for an ophthalmic lens that includes a diffractive profile disclosed herein may be fabricated utilizing a variety of methods. A method may include determining optical aberrations of a patient's eye. Measurements of a patient's eye may be made in a clinical setting, such as by an optometrist, ophthalmologist, or other medical or optical professional. The measurements may be made via manifest refraction, autorefraction, tomography, or a combination of these methods or other measurement methods. The optical aberrations of the patient's eye may be determined.

A determination of the visual range of the patient may also be determined. For example, the ability of the patient to focus on near objects (presbyopia) may be measured and determined. An amount of add power for the ophthalmic lens may be determined, as well as whether the ophthalmic lens should be bifocal, trifocal, or a greater number of focuses or an extended depth of focus lens may be determined as well.

The measurements of the patient's eye may be placed in an ophthalmic lens prescription, which includes features of an optic that are intended to address the optical aberrations of the patient's eye, as well as features that address the visual range for the patient (e.g., an amount of add power and number of focuses to be provided by the optic).

The ophthalmic lens prescription may be utilized to fabricate an optic for the ophthalmic lens. The refractive profile of the optic may be determined based on the ophthalmic lens prescription, to correct for the optical aberrations of the patient's eye. The refractive profile may also be determined to provide for the desired add power for the optic, as well as whether the optic should be bifocal, trifocal, or have a greater number of focuses or comprise an extended depth of focus optic. The refractive profile may have a region having a single add power (as shown for example in FIG. 4A), or a region having multiple different add powers (as shown for example in FIG. 5A), or regions having same add powers that are separated from each other (as shown for example in FIG. 2), or regions having different add powers that are separated from each other (as shown for example in FIG. 6A), among other configurations.

A determination may be made of the vertex shift of the distance regions caused by the regions having the add power. The determination may be made via simulation provided by a processor (such as processor 117 shown in FIG. 8), or by other calculation or testing methods. Upon the determination of the vertex shift being made, the refractive profile may be provided to vertex match the distance regions, as disclosed herein. The optic may be fabricated based on the determined refractive profile via a manufacturing assembly 119 shown in FIG. 8 or the like.

The determination of the refractive profile and the fabrication of the optic may be performed remotely from the optometrist, ophthalmologist, or other medical or optical professional that performed the measurements of a patient's eye, or may be performed in the same clinical facility of such an individual. If performed remotely, the fabricated optic may be delivered to an optometrist, ophthalmologist, or other medical or optical professional, for being provided to a patient. For an intraocular lens, the fabricated optic may be provided for implant into a patient's eye.

The fabricated optic may be a custom optic fabricated specifically for the patient's eye, or may be fabricated in a manufacturing assembly and then selected by an optometrist, ophthalmologist, or other medical or optical professional for supply to a patient, which may include implantation in the patient's eye.

Figure 8:
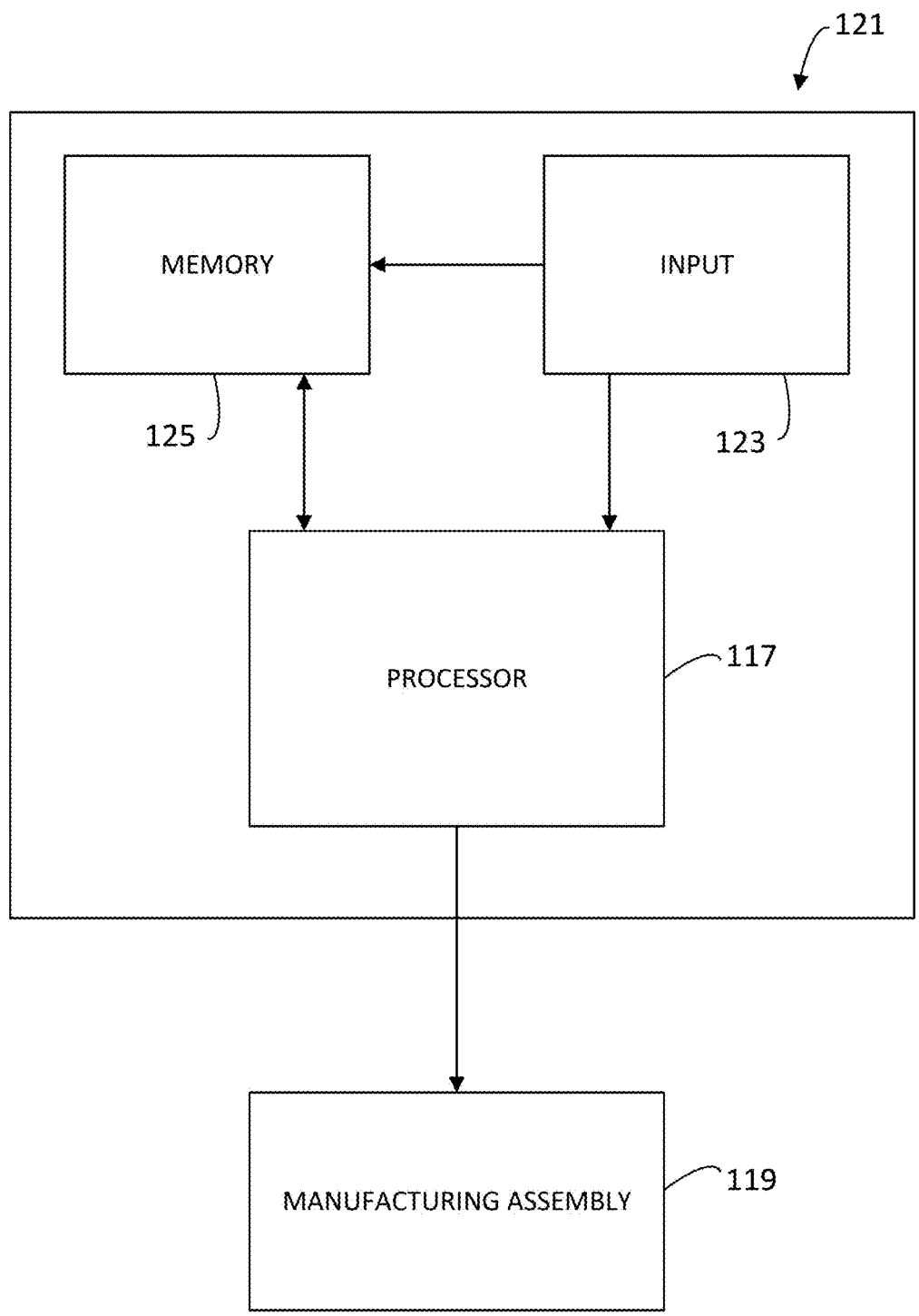
FIG. 8 illustrates an embodiment of a system.

FIG. 8 illustrates an embodiment of a system 121 that may be utilized to perform all or a portion of the methods disclosed herein. The system 121 may include a processor 117, an input 123, and a memory 125. In certain embodiments the system 121 may include a manufacturing assembly 119.

The processor 117 may comprise a central processing unit (CPU) or other form of processor. In certain embodiments the processor 117 may comprise one or more processors. The processor 117 may include one or more processors that are distributed in certain embodiments, for example, the processor 117 may be positioned remote from other components of the system 121 or may be utilized in a cloud computing environment. The memory 125 may comprise a memory that is readable by the processor 117. The memory 125 may store instructions, or features of intraocular lenses, or other parameters that may be utilized by the processor 117 to perform the methods disclosed herein. The memory 125 may comprise a hard disk, read-only memory (ROM), random access memory (RAM) or other form of non-transient medium for storing data. The input 123 may comprise a port, terminal, physical input device, or other form of input. The port or terminal may comprise a physical port or terminal or an electronic port or terminal. The port may comprise a wired or wireless communication device in certain embodiments. The physical input device may comprise a keyboard, touchscreen, keypad, pointer device, or other form of physical input device. The input 123 may be configured to provide an input to the processor 117.

The system 121 may be utilized to perform the methods disclosed herein, such as the process of determining a refractive profile of the optic. The processor 117 may be configured to determine the refractive profile to correct for the optical aberrations of the patient's eye, and to provide for the desired add power for the optic, as well as provide an optic that may be bifocal, trifocal, or have a greater number of focuses, or an extended depth of focus lens. The refractive profile may have a region having a single add power (as shown for example in FIG. 4A), or a region having multiple different add powers (as shown for example in FIG. 5A), or regions having same add powers that are separated from each other (as shown for example in FIG. 2), or regions having different add powers that are separated from each other (as shown for example in FIG. 6A), among other configurations.

The processor 117 may be configured to make a determination of the vertex shift of the distance regions caused by the regions having the add power. Upon the determination of the vertex shift being made, processor 117 may configure the refractive profile to vertex match the distance regions, as disclosed herein.

The processor 117 may provide the refractive profile to the manufacturing assembly 119, which may be configured to fabricate the optic for the ophthalmic lens based on the refractive profile. The manufacturing assembly 119 may comprise one or more apparatuses for forming the optic, and may comprise a high volume manufacturing assembly or a low volume manufacturing assembly. The manufacturing assembly 119 may be used for manufacture remote to a clinic in which measurements of the individual's eye or made, or local to such a clinic. The manufacturing assembly may include apparatuses such as lathe tools, or other lens formation devices to fabricate the optic.

In one embodiment, the processor 117 may be provided with an ophthalmic lens prescription for the individual's eye that may be provided as discussed herein. The processor 117 may receive the ophthalmic lens via the input 113. The system 121 may fabricate the optic for the ophthalmic lens based on the prescription.

The system 121 may be configured to fabricate any of the embodiments of ophthalmic lenses disclosed herein.

Beneficially, the refractive profiles disclosed herein may improve distant vision performance, without adversely affecting near and intermediate performance.

The refractive profiles disclosed herein may be provided on an anterior surface, a posterior surface, or a combination of such surfaces of the optic. The powers of the regions having the add power, and the position of such regions may be varied as desired. The lesser powers of the distance regions may be varied as desired. The optics produced may comprise multifocal, extended depth of focus, and full range optics. The features of the optics disclosed herein may be utilized by themselves, or in combination with diffractive profiles of the optics and/or with features providing for correction of chromatic aberrations (e.g., achromats, which may be diffractive).

An optic as disclosed herein may be biconvex, or possibly plano-convex, or convex-concave, or other refractive surface combinations.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

The ophthalmic lenses disclosed herein in the form of intraocular lenses are not limited to lenses for placement in the individual's capsular bag. For example, the intraocular lenses may comprise those positioned within the anterior chamber of the eye. In certain embodiments the intraocular lenses may comprise "piggy back" lenses or other forms of supplemental intraocular lenses.

Features of embodiments may be modified, substituted, excluded, or combined as desired.

In addition, the methods herein are not limited to the methods specifically described, and may include methods of utilizing the systems and apparatuses disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An intraocular lens (IOL) comprising:
an optic disposed about an optical axis and having a refractive profile including a region having an add power and a first distance vision region and a second distance vision region extending outward from the first distance vision region and being vertex matched with the first distance vision region,
wherein the first distance vision region is a central region of the optic that the optical axis extends through,
wherein the region having the add power is a near vision region positioned between the first distance vision region and the second distance vision region,
wherein the near vision region is adjacent both the first distance vision region and the second distance vision region,
wherein the second distance vision region extends outward from the near vision region, and has its vertex shifted by the presence of the near vision region,
wherein the second distance vision has a lesser power than the first distance vision region,
wherein the first distance vision region, the near vision region, and the second distance vision region form annular regions around the optical axis of the optic.

2. The intraocular lens of claim 1, wherein the second distance vision region has a lesser power than the first distance vision region in an amount of between −0.1 diopter and −0.5 diopter.

3. The intraocular lens of claim 1, wherein the add power is between 1 diopter and 5 diopter.

4. The intraocular lens of claim 1, wherein a difference in power between the first distance vision region and the second distance vision region is less than the add power.

5. The intraocular lens of claim 1, wherein the second distance vision region gradually decreases in power outward from the near vision region.

6. The intraocular lens of claim 1, wherein the region having the add power has at least two different add powers.

7. The intraocular lens of claim 1, further comprising a second near vision region having an add power extending outward from the second distance vision region.

8. The intraocular lens of claim 1, further comprising a third distance vision region extending outward from the second near vision region having the add power, the third distance vision region being vertex matched with the second distance vision region and with the first distance vision region.

9. The intraocular lens of claim 1, wherein the second distance vision region gradually decreases in power towards the third distance vision region and the third distance vision region gradually decreases in power outward from the second near vision region having the add power.

10. The intraocular lens of claim 1, wherein the optic is an extended depth of focus optic or a multifocal optic.

* * * * *